United States Patent [19]

Martin-Smith et al.

[11] 4,233,302
[45] Nov. 11, 1980

[54] AMINE DERIVATIVES AND PHARMACEUTICAL COMPOSITIONS CONTAINING THEM

[75] Inventors: Michael Martin-Smith; Barry J. Price, both of Hertford; John Bradshaw, Ware; John W. Clitherow, Sawbridgeworth, all of England

[73] Assignee: Glaxo Group Limited, London, England

[21] Appl. No.: 970,534

[22] Filed: Dec. 18, 1978

[30] Foreign Application Priority Data

Dec. 23, 1977 [GB] United Kingdom .............. 53716/77
Nov. 16, 1978 [GB] United Kingdom .............. 44778/78

[51] Int. Cl.³ .................... A61K 31/34; A61K 31/44; C07D 213/58; C07D 307/54
[52] U.S. Cl. .................................... 424/251; 548/342; 549/60; 260/326.35; 424/263; 424/267; 260/326.36; 424/270; 424/272; 260/326.37; 424/273 R; 424/274; 260/326.4; 424/275; 424/285; 260/326.5 S; 424/320; 424/321; 260/326.5 SA; 424/326; 424/330; 260/326.5 SF; 564/23; 564/27; 260/326.5 J; 564/56; 564/237; 260/326.5 B; 564/340; 564/346; 260/326.62; 260/326.8; 260/326.84; 260/326.87; 260/347.2; 260/347.3; 260/347.7; 544/298; 544/333; 544/335; 546/208; 546/209; 546/210; 546/212; 546/214; 546/230; 546/231; 546/281; 546/283; 546/300; 546/330; 546/331; 546/332
[58] Field of Search .............. 260/347.2, 347.3, 347.7, 260/326.36, 326.5 S; 424/285, 251, 263, 267, 270, 272, 273 R, 274, 275, 320, 321, 326, 330; 546/214, 283; 548/146, 215, 336; 549/60

[56] References Cited

U.S. PATENT DOCUMENTS

| | | |
|---|---|---|
| 4,002,759 | 1/1977 | Durant et al. ....................... 424/263 |
| 4,013,769 | 3/1977 | Durant et al. ....................... 424/263 |
| 4,024,260 | 5/1977 | Durant et al. ....................... 424/263 |
| 4,025,527 | 5/1977 | Durant et al. .................. 260/302 H |
| 4,034,101 | 7/1977 | Durant et al. ....................... 424/273 |
| 4,038,408 | 7/1977 | Durant et al. ....................... 424/270 |
| 4,046,907 | 9/1977 | Durant et al. ................. 424/273 R |
| 4,067,984 | 1/1978 | Durant et al. ....................... 424/263 |
| 4,080,459 | 3/1978 | Durant et al. ....................... 424/263 |
| 4,083,983 | 4/1978 | Durant et al. ....................... 424/263 |
| 4,093,729 | 6/1978 | Durant et al. ....................... 424/270 |
| 4,128,658 | 12/1978 | Price et al. ......................... 424/285 |

FOREIGN PATENT DOCUMENTS

| | | |
|---|---|---|
| 843840 | 1/1977 | Belgium . |
| 1421792 | 1/1976 | United Kingdom . |
| 1431589 | 4/1976 | United Kingdom . |
| 1497260 | 1/1978 | United Kingdom . |

*Primary Examiner*—Richard Raymond
*Attorney, Agent, or Firm*—Bacon & Thomas

[57] ABSTRACT

The invention relates to compounds of the general formula (I)

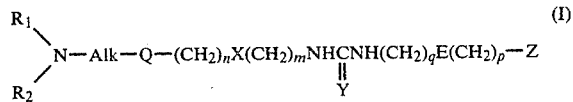

and physiologically acceptable salts, N-oxides, hydrates and bioprecursors thereof, in which Y represents =O, =S, =CHNO$_2$ or =NR$_3$ where R$_3$ represents hydrogen, nitro, cyano, lower alkyl, aryl, lower alkylsulphonyl or arylsulphonyl;

R$_1$ and R$_2$, which may be the same or different, each represent hydrogen lower alkyl, cycloalkyl, lower alkenyl, aralkyl, hydroxy, lower trifluoroalkyl, lower alkyl substituted by hydroxy, lower alkoxy, amine, lower alkylamino or dialkylamino, or R$_1$ and R$_2$ together with the nitrogen atom to which they are attached form a 5 to 7 membered heterocyclic ring which may contain other heteroatoms or the group

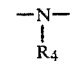

where R$_4$ represents hydrogen or lower alkyl;

Q represents a furan or thiophen ring in which incorporation into the rest of the molecule is through bonds at the 2- and 5-positions, or a benzene ring in which incorporation into the rest of the molecule is through bonds at the 1- and 3- or 1- and 4-positions;

X represents —CH$_2$, —O— or —S—;

n represents zero, 1 or 2;

m represents 2, 3 or 4;

Alk represents a straight chain alkylene group of 1 to 3 carbon atoms; (except that n is not zero when X is oxygen and Q is a furan or thiophen ring system)

q represents 2, 3 or 4 or can additionally represent zero or 1 when E is a —CH$_2$-group;

p represents zero, 1 or 2;

E represents —CH$_2$—, —O— or —S—; and

Z represents a monocyclic 5 or 6 membered carbocyclic or heterocyclic aromatic ring which may be optionally substituted by one or more groups or Z represents the group

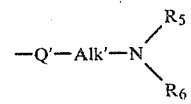

where Q' represents any of the rings defined for Q; Alk' represents any of the groups defined for Alk; and R$_5$ and R$_6$, which may be the same or different, each represent any of the groups defined for R$_1$ and R$_2$; (except that p is not zero when E is oxygen and Q' or Z is a furan or thiophen ring system).

The compounds of formula (I) show pharmacological activity as selective histamine H$_2$-antagonists.

8 Claims, No Drawings

AMINE DERIVATIVES AND PHARMACEUTICAL COMPOSITIONS CONTAINING THEM

This invention relates to new amine derivatives having a selective action on histamine receptors, to processes for the preparation thereof, to pharmaceutical compositions containing them, as well as to their use in therapeutics.

Certain novel amines have now been found which are selective $H_2$-antagonists that is they show inhibition of the secretion of gastric acid when this is stimulated via histamine receptors (Ash and Schlid—Brit. J. Pharmacol. Chemother. 1966 27, 427). Their ability to prevent the secretion of gastric juice when it is stimulated via histamine $H_2$-receptors can be demonstrated in the perfused rat stomach, using the method described in German Offenlegungsshcrift No. 2,734,070, modified by the use of sodium pentobarbitone (50 mg/kg) as anaesthetic instead of urethane and in conscious dogs equipped with Heidenhain pouches using the method described by Black et al—Nature 1972 236, 385. The compounds also antagonise the effect of histamine on the contraction frequency of isolated guinea pig right atrium. The compounds according to the invention do not modify histamine induced contractions of isolated gastrointestinal smooth muscle which are mediated via $H_1$-receptors.

Compounds with histamine $H_2$-blocking activity may be used in the treatment of conditions where there is a hypersecretion of gastric acid e.g. in gastric and peptic ulceration, as a prophylatic meaasure in surgical procedures, and in the treatment of allergic conditions where histamine is a known mediator. Thus they may be used, either alone, or in combination with other active ingredients in the treatment of allergic and inflammatory conditions such as urticaria.

The present invention provides compounds of the general formula (I)

$$R_1\!\!\diagdown\!\!N\text{—Alk—Q—}(CH_2)_nX(CH_2)_m\text{NHCNH}(CH_2)_qE(CH_2)_p\text{—Z} \quad (I)$$
$$R_2\diagup \qquad\qquad\qquad\quad \overset{\|}{Y}$$

and physiologically acceptable salts, N-oxides, hydrates and bioprecursors thereof, in which Y represents =O, =S, =CHNO$_2$ or =NR$_3$ where R$_3$ represents hydrogen, nitro, cyano, lower alkyl, aryl, lower alkylsulphonyl or arylsulphonyl;

R$_1$ and R$_2$, which may be the same or different, each represent hydrogen, lower alkyl, cycloalkyl, lower alkenyl, aralkyl, hydroxy, lower trifluoroalkyl, lower alkyl substituted by hydroxy, lower alkoxy, amino, lower alkylamino or lower dialkylamino, or R$_1$ and R$_2$ together with the nitrogen atom to which they are attached form a 5 to 7 membered heterocyclic ring which may contain other heteroatoms, e.g. oxygen, or the group

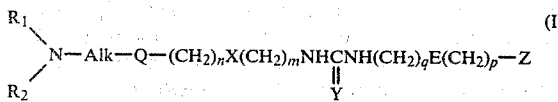

where R$_4$ represents hydrogen or lower alkyl;

Q represents a furan or thiophen ring in which incorporation into the rest of the molecule is through bonds at the 2- and 5-positions, or a benzene ring in which incorporation into the rest of the molecule is through bonds at the 1- and 3- or 1- and 4-positions;

X represents —CH$_2$—, —O— or —S—;

n represents zero, 1 or 2;

m represents 2, 3 or 4;

Alk represents a straight chain alkylene group of 1 to 3 carbon atoms; (except that n is not zero when X is oxygen and Q is a furan or thiophen ring system).

q represents 2, 3 or 4 or can additionally represent zero or 1 when E is a —CH$_2$— group;

p represents zero, 1 or 2;

E represents —CH$_2$—, —O— or —S—; and

Z represents a monocyclic 5 or 6 membered carbocyclic or heterocyclic aromatic ring which may be optionally substituted by one or more groups or Z represents the group $$-Q'-Alk'-N\diagdown\!\!\overset{R_5}{\underset{R_6}{\diagup}}$$

where Q' represents any of the rings defined for Q;

Alk' represents any of the groups defined for Alk; and

R$_5$ and R$_6$, which may be the same or different, each represent any of the groups defined for R$_1$ and R$_2$; (except that p is not zero when E is oxygen and Q' or Z is a furan or thiophen ring system).

Where Z is a heterocyclic aromatic ring it preferably contains one or more nitrogen, oxygen, or sulphur hetero atoms. For example Z may be phenyl, furyl, thienyl, pyridyl, imidazolyl, thiazolidinyl, oxazolidinyl or pyrimidinyl. The carbocyclic aromatic ring may be substituted for example, one or more of lower alkyl, optionally substituted by hydroxy, or hydroxy, amino, lower alkoxy or halogen and the heterocyclic aromatic ring may be substituted by for example, lower alkyl optionally substituted by hydroxy or halogen.

When R$_1$ and R$_2$ or R$_5$ and 6 together with the nitrogen atom to which they are attached form a heterocyclic ring, this ring is preferably a pyrrolidine or piperidine ring.

According to one aspect the invention provides compounds of the general formula (II)

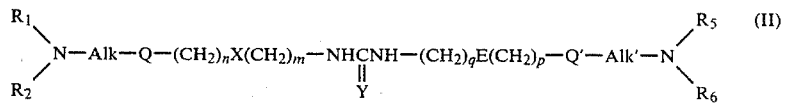

and physiologically acceptable salts, N-oxides, hydrates and bioprecursors thereof, in which Y represents =O, =S, =CHNO$_2$ or NR$_3$ where R$_3$ represents hydrogen, nitro, cyano, lower alkyl, aryl, lower alkylsulphonyl or arylsulphonyl;

R$_1$, R$_2$, R$_5$ and R$_6$ which may be the same or different, each represent hydrogen, lower alkyl, cycloalkyl, lower alkenyl, aralkyl, lower alkyl interrupted by an oxygen atom, or lower alkyl interrupted by a group $$-\underset{\underset{R_4}{|}}{N}-$$

wherein $R_4$ represents hydrogen or lower alkyl or $R_1$ and $R_2$ together with the nitroen atom to which they are attached or $R_5$ and $R_6$ together with the nitrogen atom to which they are attached form a 5 to 7 membered heterocyclic ring which may contain another heterofunction selected from oxygen or the group $$-\underset{\underset{R_4}{|}}{N}-;$$

Q and Q' which may be the same or different, each represents a furan or thiophen ring in which incorporation into the rest of the molecule is through bonds at the 2- and 5-positions, or a benzene ring in which incorporation into the rest of the molecule is through bonds at the 1- and 3-positions;

X and E, which may be the same or different, each represent $-CH_2-$, $-O-$ or $-S-$;

n and p, which may be the same or different, each represent zero, 1 or 2;

m and q, which may be the same or different, each represent 2, 3 or 4;

Alk and Alk', which may be the same or different, each represent a straight chain alkylene group of 1 to 3 carbon atoms; (except that n is not zero when X is oxygen and Q is a furan or thiophen ring system and p is not zero when E is oxygen and Q' is a furan or thiophen ring system).

According to another aspect the invention provides compounds of the general formula (III)

$$R_1\diagdown_{N-Alk-Q-(CH_2)_nX(CH_2)_mNH\underset{\underset{Y}{\|}}{C}NH(CH_2)_qE(CH_2)_p-Z'} \quad (III)$$
$$R_2\diagup$$

and physiologically acceptable salts, N-oxides, hydrates and bioprecursors thereof, in which Y represents $=O$, $=S$, $=CHNO_2$ or $=NR_3$ where $R_3$ represents hydrogen, nitro, cyano, lower alkyl, aryl, lower alkylsulphonyl or arylsulphonyl; $R_1$ and $R_2$, which may be the same or different, each represent hydrogen, lower alkyl, cycloalkyl, lower alkenyl, aralkyl, lower alkyl interrupted by an oxygen atom, lower alkyl interrupted by $$-\underset{\underset{R_4}{|}}{N}-$$

in which $R_4$ represents hydrogen or lower alkyl, or $R_1$ and $R_2$ together with the nitrogen atom to which they are attached form a 5 to 7 membered heterocyclic ring which may contain the further heterofunction oxygen or $$-\underset{\underset{R_4}{|}}{N}-;$$

Q represents a furan or thiophen ring in which incorporation into the rest of the molecule is through bonds at the 2- and 5-positions, or a benzene ring in which incorporation into the rest of the molecule is through bonds at the 1- and 3- or 1 and 4-positions;

X represents $-CH_2-$, $-O-$ or $-S-$;

n represents zero or 1;

m represents 2, 3 or 4;

Alk represents a straight chain alkylene group of 1 to 3 carbon atoms; (except that n is not zero when X is oxygen and Q is a furan or thiophen ring system);

q represents 2, 3 or 4 or can additionally represent zero or 1 when E is $-CH_2-$ group;

p represents zero 1 or 2;

E represents $-CH_2-$, $-O-$ or $-S-$;

Z' represents a monocyclic carbocyclic or heterocyclic aromatic ring which may be optionally substituted by one or more groups; (except that p is not zero when E is oxygen and Z' is furyl or thienyl).

The term "alkyl" means a straight or branched alkyl group and the term "lower" as applied to "alkyl" means that the group has preferably 1 to 6 carbon atoms, and in particular 1 to 4 carbon atoms, e.g. methyl or ethyl and when applied to "alkenyl" that the group has preferably 3 to 6 carbon atoms. The term "cycloalkyl" means that the ring has 3 to 7 carbon atoms, preferably 5 or 6 carbon atoms. The term "aryl" as a group or part of a group preferably means phenyl or substituted phenyl for example phenyl substituted with one or more alkyl, alkoxy or halogen groups. The alkyl portion of the term "aralkyl" preferably has 1 to 3 carbon atoms, e.g. benzyl or phenethyl.

The compounds of formula (I) can exhibit tautomerism and optical isomerism and the formula is intended to cover all tautomers and optical isomers and mixtures thereof.

The invention includes the compounds of formula (I) in the form of physiologically acceptable salts with inorganic and organic acids. Particularly useful salts include hydrochlorides, hydrobromides and sulphates; acetates, maleates and fumarates. The compounds and their salts may also form hydrates which hydrates are also to be considered as part of the invention.

The compounds according to the invention may be formulated for administration in any convenient way and the invention includes within its scope pharmaceutical compositions containing at least one compound according to the invention adapted for use in human or veterinary medicine. Such compositions may be formulated in a conventional manner using one or more pharmaceutically acceptable carriers or excipients. Such compositions may also if required contain other active ingredients, e.g. anti-histamines having selective $H_1$-blocking activity.

Thus the compounds according to the invention may be formulated for oral, buccal, topical, parenteral or rectal administration.

The compounds of the invention may be formulated for parenteral administration by bolus injection or continuous infusion. Formulations for injection may be presented in unit dosage form in ampoules, or in multidose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water before use.

For oral administration, the pharmaceutical composition may take the form of for example, tablets, capsules, powders, solutions, syrups or suspensions prepared by conventional means with acceptable excipients. For buccal administration the composition make take the form of tablets or lozenges formulated in conventional manner.

The compounds of the invention may also be formulated in rectal compositions such as suppositories or retention enemas, e.g. containing conventional suppository bases such as cocoa butter or other glycerides.

For topical application, the compounds of the invention may be formulated as ointments, creams, gels, lotions, powders or sprays. Ointments and creams may, for example, be formulated with an aqueous or oily base with the addition of suitable pharmaceutical excipients. Lotions may be formulated with an aqueous or oily base and will include the necessary adjustments to ensure pharmaceutically acceptable products. Spray compositions may, for example, be formulated as aerosols which may be pressurised by means of a suitable agent such as dichlorofluoromethane or trichlorofluoromethane or may be delivered by means of a hand operated atomiser.

For internal administration a convenient daily dose of the compounds according to the invention would be of the order of 50 mg to 2 g per day, for example 100 mg to 1500 mg per day.

Compositions containing the compounds according to the invention may be suitable for either human or veterinary use.

Preferred compounds according to the invention are compounds of formula (I) in which Y represents $=O$, $=S$, $=CHNO_2$, $=NCN$ or $=NSO_2CH_3$;

$R_1$ and $R_2$, which may be the same or different, each represent hydrogen or lower alkyl or $R_1$ and $R_2$ together with the nitrogen atom to which they are attached form a 5 to 7 membered heterocyclic ring;

Q represents a furan or thiophen ring in which incorporation into the rest of the molecule is through bonds at the 2- and 5-positions or a benzene ring in which incorporation into the rest of the molecule is through bonds at the 1- and 3-positions;

X represents —O— or —S—; n represents zero or 1; m represents 2 or 3; Alk represents —$CH_2$—;

q represents zero, 1 2 or 3; p represents zero, 1 or 2; E represents —$CH_2$—, —O— or —S—; and Z represens furyl, lower alkyl substituted and imidazolyl, phenyl, hydroxyalkyl substituted furyl, pyridyl, hydroxyalkyl substituted phenyl or —Q'—Alk—$NR_5R_6$ where Q' represents a furan or thiophen ring in which incorporation into the rest of the molecule is through bonds at the 2- and 5-positions or a benzene ring in which incorporation into the rest of the molecule is through bonds at the 1- and 3-positions; Alk' represents —$CH_2$—; and $R_5$ and $R_6$ which may be the same or different, each represent hydrogen or lower alkyl or $R_5$ and $R_6$ together with the nitrogen atom to which they are attached form a 5 to 7 membered heterocyclic ring.

Preferably Y represents $=CHNO_2$ or $=NCN$. Preferably m+n is 3 or 4. Preferably q+p is 3 or 4 when Z is oxygen or sulphur and q+p is zero, 1, 2, 3 or 4 when E is —$CH_2$—. Preferably when Q and/or Q' represent a benzene ring then n is zero and X is oxygen.

Particularly preferred compounds are

N-[2-[[5-[(dimethylamino)methyl]-2-furanylmethyl]thio]ethyl]-N'-[[2-(furanylmethyl)-thio]ethyl]-2-nitro-1,1-ethenediamine;

N-[3-[5-[(dimethylamino)methyl]-2-furanylmethoxy]propyl]-2-nitro-N'-[2-[(3-pyridinylmethyl)thio]ethyl]1,1-ethenediamine;

N-[2-[[5-[(dimethylamino)methyl]-2-furanylmethyl]thio]ethyl]-N'-[3-[3-(hydroxymethyl)phenoxy]propyl]-2-nitro-1,1-ethenediamine;

N-[2-[[5-[(dimethylamino)methyl]-2-furanylmethyl]thio]ethyl]-2-nitro-N'-[2-[(3-pyridinylmethyl)thio]ethyl]1,1-ethenediamine;

N,N'-bis[2-[[5-[(methylamino)methyl]-2-furanylmethyl]thio]ethyl]-2-nitro-1,1-ethenediamine;

N''-cyano-N,N'-bis[3-[3-[(dimethylamino)methyl]phenoxy]propyl]guanidine;

2-nitro-N,N'-bis-[3-[3-[(1-pyrrolidinyl)methyl]phenoxy]propyl]-1,1-ethenediamine;

N-[2 [[5-[(dimethylamino)methyl]-2-furanylmethyl]thio]ethyl]-N'-[3-[3-[(dimethylamino)methyl]phenoxy]propyl]-2-nitro-1,1-ethenediamine;

N-[2-[[5-[(dimethylamino)methyl]-2-furanylmethyl]thio]ethyl]-N'-[2-[[5-[(dimethylamino)methyl]-2-thienylmethyl]thio]ethyl]-2-nitro-1,1-ethenediamine;

N-[2-[[5-[(dimethylamino)methyl]-2-furanylmethyl]thio]ethyl]-N'-[2-[[5-[(methylamino)methyl]-2-furanylmethyl]thio]ethyl]-2-nitro-1,1-ethenediamine;

N-[2-[[5-[(dimethylamino)methyl]-2-furanylmethyl]thio]ethyl]-N'-[2-[[5-[[hydroxy(methyl)amino]methyl]-2-furanylmethyl]thio]ethyl]-2-nitro-1,1-ethenediamine;

N-[3-[3-[(dimethylamino)methyl]phenoxy]propyl]-N'-[2-[[5-[(methylamino)methyl]-2-furanylmethyl]thio]ethyl]-2-nitro-1,1-ethenediamine;

N''-cyano-N-[3-[3-[(dimethylamino)methyl]phenoxy]propyl]-N'-[2-[[5-[(1-pyrrolidinyl)methyl]-2-furanylmethyl]thio]ethyl]guanidine;

N-[2-[[5-[(dimethylamino)methyl]-2-furanylmethyl]thio]ethyl]-2-nitro-N'-[3-[3-[(1-pyrrolidinyl)methyl]phenoxy]propyl]-1,1-ethenediamine.

It will be appreciated that in the methods for the preparation of compounds of formula (I) given below, that for certain reaction steps it may be necessary to protect various reactive substituents in the starting materials for a particular reaction and subsequently to remove the protecting group after completion of the reaction. Such protection and subsequent deprotection may be particularly pertinent where $R_1$ and/or $R_2$ in intermediates used to prepare compounds of formula (I) are hydrogen atoms and/or when Z in certain intermediates contains a group bearing a replaceable hydrogen atom, i.e. $R_5$ and/or $R_6$ are hydrogen atoms, or bears a hydroxyl or hydroxyalkyl, or a primary or secondary amino substituent. Standard protection and deprotection procedures can be employed:

for example formation of phthalimide (in the case of primary amines), N-benzyl, N-benzyloxycarbonyl, or N-trichloroethoxycarbonyl derivatives. Subsequent cleavage of the protecting group is achieved by conventional procedures. Thus a phthalimide group may be cleaved by treatment with a hydrazine e.g. hydrazine hydrate or a primary amine, for example methylamine; N-benzyl or N-benzyloxycarbonyl derivatives may be cleaved by hydrogenolysis in the presence of a catalyst, e.g. palladium, and N-trichloroethoxycarbonyl derivatives may be treated with zinc dust.

Compounds of formula (I) in which q is the same as m, E is the same as X, p is the same as n and Z is

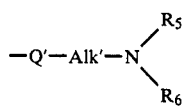

with Q' the same as Q, Alk' the same as Alk, $R_5$ the same as $R_1$ and $R_6$ the same as $R_2$, can be prepared from a primary amine of formula (IV)

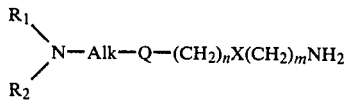 (IV)

in which $R_1$, $R_2$, Alk, Q, n, X and m are as defined in formula (I), by reaction with a compound capable of introducing the group

between the two amine residues derived from formula (IV). This reaction may be carried out in the absence or presence of a solvent, e.g. water or an ester e.g. ethyl acetate or an ether e.g. dioxan, conveniently at a temperature from ambient to reflux.

Compounds which are capable of introducing the group

may be of the formula (V)

 (V)

where P is a leaving group such as halogen, thioalkyl, alkoxy or 3,5-dimethylpyrazolyl when Y is a group $NR_3$ or $CHNO_2$, or when Y is an oxygen or sulphur atom P may be a halogen atom or a 1,3-imidazolyl group.

Two molecular equivalents of the amine (IV) react with one molecular equivalent of the compound of formula (V).

Compounds of formula (I) can also be prepared by reacting an amine of formula (IV) in which $R_1$, $R_2$, Alk, Q, n, X and m are as defined in formula (I) (and wherein, if $R_1$ and $R_2$ are hydrogen, the group $-NR_1R_2$ is protected), with a compound capable of converting the group $-NH_2$ into the group

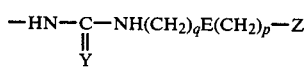

in which Y, q, E, p and Z are as defined in formula (I). Alternatively an amine of formula (VI)

 (VI)

in which Z, p, E and q are as defined in formula (I) (and any primary or secondary amino group or hydroxyl group within group Z are protected), can be reacted with a compound capable of converting the group $-NH_2$ into the group

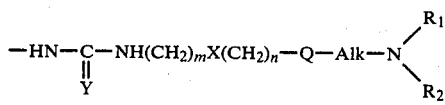

in which Y, m, X, n, Q, Alk, $R_1$ and $R_2$ are as defined in formula (I).

Compounds which are capable of converting the $NH_2$ group into the group

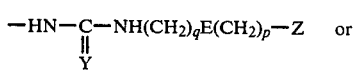 or

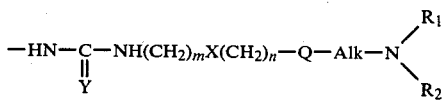

where Y is oxygen or sulphur are isocyanates or isothiocyanates of the formula (VII) or (VIII)

$Z-(CH_2)_pE(CH_2)_qNCY$     (VII)

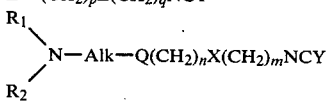 (VIII)

The reaction with the isocyanates or isothiocyanate may be carried out by allowing the amine and isocyanate or isothiocyanate to stand in a solvent such as tetrahydrofuran, as acetonitrile. The isocyanate (VII) or isothiocyanate (VIII) can be prepared by established methods from the corresponding amine (IV), e.g. isothiocyanate can be prepared by treating the amine with carbon disulphide with decomposition of the intermediate so formed with mercuric chloride and a base e.g. triethylamine or with a chloroformate ester e.g. ethyl chloroformate; the isocyanate may be prepared by treating the amine with phosgene and a base, for example, triethylamine.

Where Y is $=CHNO_2$ or $=NR_3$ a compound of the formula (IX)

$Z-(CH_2)_pE(CH_2)_qNHC-L$     (IX)
                           ‖
                           Y can be used to introduce the group

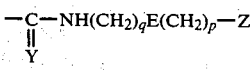

into an amine of formula (IV). L is a leaving group, such as thioalkyl for example thiomethyl or alkoxy, for example ethoxy. Similarly a compound of formula (X)

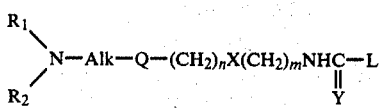

can be used to introduce the group

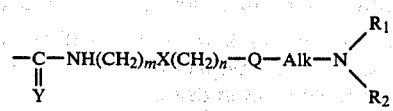

into an amine of formula (VI). The reaction can be carried out by heating the reactants in the presence or absence of a solvent e.g. acetonitrile at a temperature of e.g. 100° to 120° C. Alternatively an amine (IV) or (VI) and a compound (XI) or (XII) respectively $$Z-(CH_2)_pE(CH_2)_q-NHC-L \quad (XI)$$
$$\| \quad CHNO_2$$

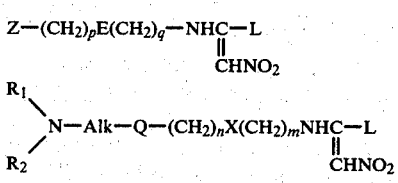

may be stirred in aqueous solution at room temperature.

Compounds of formula (IX) and (X) where Y is $=CHNO_2$ or $=NR_3$ can be prepared by reacting the amine (VI) or (IV) with a compound of the formula (XIII) or (XIV) respectively

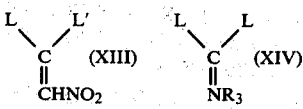

in which L is a leaving group as defined above and L' is as defined for L or may, in addition be a group

where A represents an alkyl group. The reaction may be carried out in a solvent such as ether, acetonitrile, dioxan or ethyl acetate at a temperature from ambient to reflux.

Compounds of formula (I) in which n is 1, X is sulphur and other groups are as defined in formula (I), may be prepared from compounds of formulae (XV) or (XVI) by reaction with a thiol of formula (XVII).

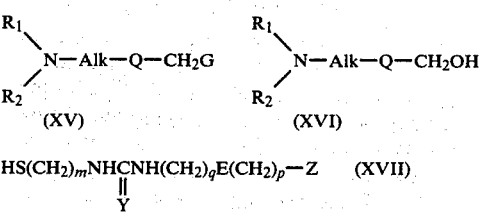

$$HS(CH_2)_mNHCNH(CH_2)_qE(CH_2)_p-Z \quad (XVII)$$
$$\| \quad Y$$

In the above formula (XV) G represents a leaving group e.g. halogen, e.g. bromine, or an acyloxy, e.g. acetoxy group. In the case of compounds in which $R_1$ and $R_2$ are hydrogen, the amino group $NR_1R_2$ is protected in compounds of formulae (XV) and (XVI) as in the case of a primary amine, for example as a phthalimido group, in which case the protecting group may be cleaved at an appropriate stage using a primary amine e.g. methylamine.

Compounds of formula (I) in which p is 1 and E is sulphur may be prepared from compounds of formula (XVIII) or (XIX) by reaction with a thiol of formula (XX):

$$Z-CH_2G \qquad Z-CH_2OH$$
$$(XVIII) \qquad (XIX)$$

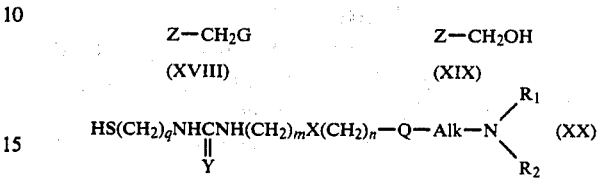

any amino groups in the group Z within compounds (XVIII) and (XIX) being protected. In the above formula (XVIII) G represents a leaving group as defined above.

The reaction between a thiol (XVII) and a compound of formula (XV) or between a thiol (XX) and a compound of formula (XVIII) where Z is as defined in formula (I) is preferably carried out in the presence of a strong base e.g. sodium hydride at room temperature in an organic solvent e.g. dimethylformamide. The reaction between a thiol (XVII) and a compound of formula (XVI) or between a thiol (XX) and a compound of formula (XIX) is preferably carried out at 0° C. in a mineral acid e.g. concentrated hydrochloric acid. The starting materials of formulae (XV) or (XVIII) may be prepared from alcohols of formulae (XVI) or (XIX) by established methods.

Compounds of formula (I) in which Q is a furan ring, Alk is methylene, Z is other than furyl and Y is $=NR_3$ can be prepared from compounds of the formula (XXI):

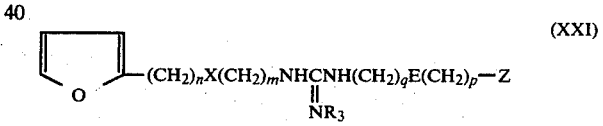

by a Mannich reaction with formaldehyde and a secondary amine or a salt of a primary amine or a secondary amine.

Similarly compounds of formula (I) in which Z is

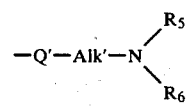

and Q' is a furan ring, Alk' is methylene and Y is $=NR_3$ can be prepared from compounds of formula (XXII)

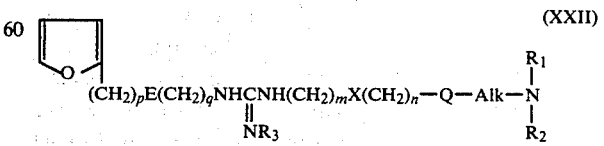

by a Mannich reaction with formaldehyde and a secondary amine or a salt of a primary amine or a secondary amine. For example, the $(CH_3)_2NCH_2$-group can be introduced on to the 5-position of the furan ring of a compound of formula (XXI) or (XXII) using dimethylamine and formaldehyde. The process may be carried out by reacting the amine salt with aqueous formaldehyde and the compound of formula (XXI) or (XXII) or by refluxing the amine salt in a suitable solvent, e.g. ethanol, with paraformaldehyde and the compound of formula (XXI) or (XXII).

Compounds of formula (I) in which $R_1$ and $R_2$ are both methyl, Q is a furan or thiophen ring, Y is other than $=CHNO_2$ and Z is other than furyl or thienyl can be prepared by treating a compound of formula (XXIII)

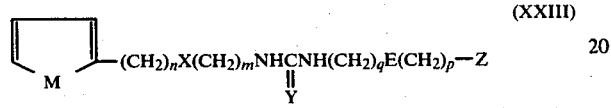

(XXIII)

in which Y is other than $=CHNO_2$, M represents oxygen or sulphur with the reagent of the formula (XXIV)

(XXIV)

in a solvent e.g. in acetonitrile at reflux temperature.

Similarly compounds of formula (I) in which Z

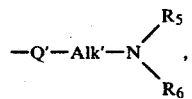

$R_5$ and $R_6$ are both methyl, Q' is a furan or thiophen ring and Y is other than $=CHNO_2$ can be prepared by treating a compound of formula (XXV)

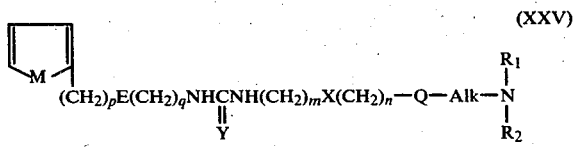

(XXV)

with the reagent (XXIV) under the conditions specified above.

When the groups $R_1$ and $R_2$ or $R_5$ and $R_6$ in compounds of formula (I) are hydrogen they may be converted into alkyl or aralkyl groups by reaction with, for example, an alkyl or aralkyl halide in the presence of sodium iodide and an appropriate base e.g. potassium carbonate, in a suitable solvent, for example methanol.

Where the product of any of the above processes is a free base and a salt is required, the salt may be formed in a conventional manner.

The invention is illustrated but not limited by the following Examples.

EXAMPLE 1

N-[2-[[5-[(Dimethylamino)methyl]-2-furanylmethyl]thio]ethyl]-N'-[[2-(furanylmethyl)thio]ethyl]-2-nitro-1,1-ethenediamine

A.

N,N-Dimethyl-5-[[[2-[(1-methylthio-2-nitroethenyl)amino]ethyl]thio]methyl]-2-furanmethanamine oxalate A solution of 1,1-bis(methylthio)-2-nitroethene (19.8 g) and 5-[[(2-aminoethyl)thio]methyl]-N,N-dimethyl-2-furanmethanamine (6.42 g) in dry dioxan (120 ml) was heated at 80° C. for 6 hours. Oxalic acid (3.8 g) in dry dioxan (40 ml) was added and the crystalline solid which separated was filtered, washed with dioxan and dried to give the title compound (12.55 g) m.p. 140°–143° C.

B.

N,N-Dimethyl-5-[[[2-[(1-methylthio-2-nitroethenyl)amino]ethyl]thio]methyl]-2-furanmethanamine To N,N-dimethyl-5-[[[2-[(1-methylthio-2-nitroethenyl)amino]ethyl]thio]methyl]-2-furanmethanamine oxalate, formed from 1,1-bis(methylthio)-2-nitroethene (29.7 g), 5-[[(2-aminoethyl)thio]methyl]-N,N-dimethyl-2-furanmethanamine (9.63 g) and oxalic acid (5.7 g) as previously described, was added excess 2 M aqueous potassium carbonate. The suspension was extracted with ethyl acetate and the dried extract evaporated in vacuo to yield an oil which on trituration with ether yielded the title compound (10.5 g) m.p. 71° C.

C.

N-[2-[[5-[(Dimethylamino)methyl]-2-furanylmethyl]thio]ethyl]-N'-[[2-(furanylmethyl)thio]ethyl]-2-nitro-1,1-ethenediamine A mixture of N,N-dimethyl-5-[[[2-[(1-methylthio-2-nitroethenyl)amino]ethyl]thio]methyl]-2-furanmethanamine (3.3 g) and 2-[(2-furanylmethyl)thio]thanamine (1.57 g) was heated at 120° C. for 3 hours. The oily product was subjected to column chromatography (silica/methanol-0.88 ammonia, 100:1) and the appropriate eluate evaporated to dryness in vacuo. The oily residue was dissolved in chloroform (75 ml), the solution dried (potassium carbonate) and evaporated in vacuo to give the title compound as the hydrate as a yellow oil (2.2 g).

Found: C,49.9; H,6.2; N,11.9. $C_{19}H_{28}N_4O_4S_2.H_2O$ requires: C,49.8; H,6.6; N,12.2%.

TLC (Silica/methanol-0.88 ammonia 79:1) Rf 0.62.

EXAMPLE 2

N-[2-[[5-[(Dimethylamino)methyl]-2-furanylmethyl]thio]ethyl]-N'-[2-[(4-methyl-1H-imidazol-5-yl)methyl)thio]ethyl]-2-nitro-1,1-ethene diamine A mixture of potassium hydroxide (0.184 g), 4-methyl-5-[(2-aminoethyl)thiomethyl]imidazole dihydrochloride (0.4 g) and N,N-dimethyl[[[2-[(1-methylthio-2-nitroethenyl)amino]ethyl]thio]methyl]-2-furanmethanamine (1.14 g) in methanol (5 ml) was evaporated to dryness in vacuo and the residue heated at 98°–100° C. for 8 hours. The semi-solid was extracted with hot acetonitrile (3×10 ml) and the combined extracts were evaporated to dryness to give an oil which was subjected to column chromatography (silica/methanol-0.88 ammonia 79:1). The appropriate eluate was evaporated to dryness to give the title compound as a hemihydrate as a semi-solid (0.43 g).

Found: C,49.6; H,6.9; N,17.8%. $C_{19}H_{30}N_6O_3S_2\cdot\frac{1}{2}H_2O$ requires: C,49.2; H,6.7; N,18.1%.

TLC (Silica/methanol-0.88 ammonia 79:1) Rf 0.45.

EXAMPLE 3

N-[3-[3-[(Dimethylamino)methyl]phenoxy]propyl]-2-nitro-N'-(2-phenylethyl)-1,1-ethenediamine, hydrochloride

A.

N,N-dimethyl-3-[3-[(1-methylthio-2-nitroethenyl)amino]propoxy]benzenemethanamine 3-(3-Aminopropoxy)-N,N-dimethylbenzenemethanamine (10 g) and 1,1-bis-(methylthio)-2-nitroethane (16 g) were heated under reflux in tetrahydrofuran for 19 hours. Oxalic acid dihydrate (1.3 g) was added and the resulting precipitate was discarded. The solvent was removed to leave the title compound as a crystalline solid (10 g) m.p. 59°–63°.

B.

N-[3-[3-[(Dimethylamino)methyl]phenoxy]propyl]-2-nitro-N'-(2-phenylethyl)-1,1-ethenediamine, hydrochloride A mixture of N,N-dimethyl-3-[3-[(1-methylthio-2-nitroethenyl)amino]propoxy]benzenemethanamine (0.81 g) and 2-phenylethylamine (0.3 g) was stirred at room temperature in ethanol (10 ml) for 65 hr. The ethanol was evaporated to give an orange oil which was dissolved in 2 N ethanolic hydrogen chloride and treated with ethyl acetate. The title compound crystallised as a white solid (0.72 g) m.p. 142°–144.5° C.

TLC silica; ethyl acetate:isopropanol:water:0.88 ammonia (25:15:8:2) Rf 0.7.

EXAMPLE 4

(i)

N-[2-[[5-[(Dimethylamino)methyl]-2-furanylmethyl]thio]ethyl]-N'-[2-[[5-(hydroxymethyl)-2-furanylmethyl]thio]ethyl]-2-nitro-1,1-ethenediamine

A.

2-[2-[(2-Furanylmethyl)thio]ethyl]-1H-isoindole-1,3(2H)-dione

Furfuryl mercaptan (11.4 g) was added to a stirred solution of sodium (2.41 g) in ethanol (100 ml). After 5 mins a solution of 2-(2-bromoethyl)-1H-isoindole[2H]-dione (25.4 g) in ethanol (200 ml) was added and the mixture stirred for 12 hr. The mixture was poured into water (1 liter), the precipitate collected and crystallised from aqueous methanol to give the title compound as white needles (19.3 g) m.p. 59°–61°.

B.

2-[2-[(5-Formyl-2-furanylmethyl)thio]ethyl]-1H-isoindole-1,3(2H)-dione

Phosphorus oxychloride (6.4 g) was added to a stirred solution of 2-[2-[(2-furanylmethyl)thio]ethyl]-1H-isoindole-1,3(2H)-dione (6.0 g) in dry dimethylformamide. After stirring for 2 hr at 0° C. and at room temperature for 12 hr, the mixture was poured into stirred ice-cold water (500 ml). The precipitated solid was collected and crystallised from propan-2-ol yielding the title compound as brown micro-needles (5.6 g) m.p. 77°–79°.

C.

2-[2-[[5-(Hydroxymethyl)-2-furanylmethyl]thio]ethyl]-1H-isoindole-1,3(2H)-dione

Sodium borohydride (165 mg) was added in portions over a period of 10 mins to a solution of 2-[2-[(5-formyl-2-furanylmethyl)thio]ethyl]-1H-isoindole-1,3(2H)-dione (5.0 g) in methanol (100 ml) at 0° C. After stirring for 45 mins, acetic acid (1 ml) was added and the mixture evaporated. Water (100 ml) was added and the solid that precipitated extracted into ethyl acetate (2×150 ml). The ethyl acetate extracts were dried (magnesium sulphate) and evaporated yielding an oil which solidified on trituration in light petroleum (b.p. 60°–80° C.). Crystallisation from methyl acetate-light petroleum (b.p. 60°–80° C.) afforded the title compound as a light, white solid (4.05 g) m.p. 82.5°–84° C.

D.

2-[[5-(Hydroxymethyl)-2-furanylmethyl]thio]ethanamine

A solution of 2-[2-[[5-(hydroxymethyl)-2-furanylmethyl]thio]ethyl]-1H-isoindole-1,3(2H)-dione, (5.0 g) in ethanol (50 ml) was stirred in the presence of methylamine (33% in ethanol) (15 ml) for 15 mins. The residue was subjected to column chromatography (silica/methanol-ethyl acetate 1:1, then methanol) and the appropriate eluates were evaporated. Chloroform (50 ml) was added to the oily product, the solution dried (anhyd. magnesium sulphate) and evaporated yielding the title compound as a pale yellow oil (1.35 g).

TLC (silica/methanol-0.88 ammonia 79:1) Rf 0.38.

E.

N-[2-[[5-[(Dimethylamino)methyl]-2-furanylmethyl]thio]ethyl]-N'-[2-[[5-(hydroxymethyl)-2-furanylmethyl]thio]ethyl]-2-nitro-1,1-ethenediamine A mixture of 2-[[5-(hydroxymethyl-2-furanylmethyl]thio]ethanamine (1.3 g) and N,N-dimethyl-5-[[[2-[(1-methylthio-2-nitroethenyl)amino]ethyl]thio]methyl]-2-furanmethanamine (2.18 g) was heated at 100° C. for 3 hr. The resulting orange gum was subjected to column chromatography (silica/methanol) and the appropriate eluates were evaporated giving the title compound as a sesquihydrate as a pale yellow oil (2.8 g).

TLC (silica, methanol-0.88 ammonia 79:1) Rf 0.48.

Found: C, 48.5; H, 6.7; N, 11.3. $C_{20}H_{30}N_4O_5S_2\cdot 1\frac{1}{2}H_2O$ requires: C, 48.3; H, 6.7; N, 11.3%.

Similarly prepared as in E were:

(ii) N-[2-[[5-[(Dimethylamino)methyl]-2-furanylmethylthio]ethyl]-2-nitro-N'-[2-[(phenylmethyl)thio]ethyl]-1,1-ethenediamine (0.88 g) from N,N-dimethyl-5-[[[2-[(1-methylthio-2-nitroethenyl)amino]ethyl]thio]methyl]-2-furanmethanamine (1 g) and 2-[(phenylmethyl)thio]ethanamine (0.55 g) at 98°–100° for 1.5 hours.

Found: C, 56.0; H, 7.1; N, 12.1. $C_{21}H_{30}N_4O_3S_2$ requires: C, 56.0; H, 6.7; N, 12.4%.

TLC (silica/methanol-0.88 ammonia 79:1) Rf 0.65.

(iii) N-[2-[[5-[(Dimethylamino)methyl]-2-furanylmethyl]thio]ethyl]-2-nitro-N'-(2-phenylethyl)-1,1-ethenediamine (0.73 g) m.p. 64°–65° from N,N-dimethyl-5-[[[2-[(1-methylthio-2-nitroethenyl)amino]ethyl]thio]methyl]-2-furanmethanamine (1.5 g) and 2-phenylethanamine (0.79 g) at 98°–100° for 20 mins.

Found: C, 59.5; H, 7.2; N, 14.1. $C_{20}H_{28}N_4O_3S$ requires: C, 59.4; H, 7.0; N, 13.9%.

(iv) N-[2-[[5-[(Dimethylamino)methyl]-2-furanylmethyl]thio]ethyl]-2-nitro-N'-[2-(2-pyridinyl)ethyl]-1,1- ethenediamine (1.35 g) as its hemihydrate from N,N-dimethyl-5-[[[2-[(1-methylthio-2-nitroethenyl)amino]ethyl]thio]methyl]-2-furanmethanamine (1.5 g) and 2-(2-pyridinyl)ethanamine (0.61 g) at 98°–100° for 4 hours.

Found: C, 54.9; H, 6.8; N, 17.0. $C_{19}H_{27}N_5O_3S.\frac{1}{2}H_2O$ requires: C, 55.0; H, 6.8; N, 16.9%.

TLC (silica/methanol-0.88 ammonia 79:1) Rf 0.49.

(v) N-[2-[[5-[(Dimethylamino)methyl]-2-furanylmethyl]thio]ethyl]-2-nitro-N'-(3-pyridinylmethyl)-1,1-ethenediamine (0.83 g) as its monohydrate from N,N-dimethyl-5-[[[2-[(1-methylthio-2-nitroethenyl)amino]ethyl]thio]methyl]-2-furanmethanamine (1.5 g) and 3-pyridinylmethanamine (0.54 g) at 98°–100° for 6 hours.

Found: C, 52.8; H, 6.6; N, 17.0. $C_{18}H_{25}N_5O_3S.H_2O$ requires: C, 52.8; H, 6.6; N, 17.1%.

TLC (silica/methanol-0.88 ammonia 79:1) Rf 0.37.

(vi) N-[3-[3-[(Dimethylamino)methyl]phenoxy]propyl]-2-nitro-N'-(3-phenylpropyl)-1,1-ethenediamine hydrochloride (0.34 g) m.p. 146°–147° from N,N-dimethyl-3-[3-[(1-methylthio-2-nitroethenyl)amino]propoxy]benzenemethanamine (0.81 g) and 3-phenylpropanamine (0.34 g) at 70° for 5 hours followed by conversion of the base into the hydrochloride salt in ethanol-ethyl acetate.

Found: C, 62.0; H, 7.7; N, 12.6. $C_{23}H_{32}N_4O_3.HCl$ requires: C, 61.5; H, 7.4; N, 12.5%.

(vii) N-[3-[3-[(Dimethylamino)methyl]phenoxy]propyl]-2-nitro-N'-(phenylmethyl)-1,1-ethenediamine hydrochloride (0.63 g) m.p. 137°–140° from N,N-dimethyl-3-[3-[(1-methylthio-2-nitroethenyl)amino]propoxy]benzenemethanamine (0.81 g) and benzenemethanamine (0.26 g) at 70° for 5 hours followed by conversion of the base into the hydrochloride salt is ethanol.

Found: C, 59.8; H, 6.9; N, 13.0. $C_{21}H_{28}N_4O_3.HCl$ requires: C, 59.9; H, 6.9; N, 13.3%.

TLC (silica/ethyl acetate-isopropanol-water-0.88 ammonia 25:15:8:2) Rf 0.75.

(viii) N-[2-[[5-[(Dimethylamino)methyl]-2-furanylmethyl]thio]ethyl]-2-nitro-N'-[2-[(3-pyridinylmethyl)thio]ethyl]-1,1-ethenediamine (0.67 g) from N,N-dimethyl-5-[[[2-[(1-methylthio-2-nitroethenyl)amino]ethyl]thio]methyl]-2-furanmethanamine (1.66 g) and 2-[(3-pyridinylmethyl)thio]ethanamine (1.26 g) at 98°–100° for 2 hours.

TLC (silica/methanol-0.88 ammonia 79:1) Rf 0.5.

Found: C, 52.3; H, 6.5; N, 15.2. $C_{20}H_{29}N_5O_3S_2.\frac{1}{2}H_2O$ requires: C, 52.1; H, 6.6; N, 15.2%.

EXAMPLE 5

N-[2-[[[5-(Dimethylamino)methyl]-2-furanylmethyl]thio]ethyl]-N'-[3-[3-(hydroxymethyl)phenoxy]propyl]-2-nitro-1,1-ethenediamine

A.

2-[3-[(3-Hydroxymethyl)phenoxy]propyl]-1H-isoindole-1,3(2H)-dione

Sodium borohydride (0.325 g) was added portionwise to a stirred solution of 2-[3-[3-(formyl)phenoxy]propyl]-1H-isoindole-1,3(2H)-dione (9 g) in methanol (200 ml) at 5° during 1 hr. After 1 hr acetic acid (5 ml) was added, the solution evaporated and the residue dissolved in ethyl acetate (250 ml). The solution was washed with water, the ethyl acetate phase dried (magnesium sulphate) and evaporated to give an oil which was chromatographed (silica/ethyl acetate-light petroleum 60°–80°, 1:1). The appropriate eluate was evaporated to dryness and the solid residue was crystallised from ethyl acetate-light petroleum (80°–100°) to give the title compound (4 g) m.p. 81°–83°.

B. 3-[(3-Hydroxymethyl)phenoxy]propanamine

A solution of hydrazine hydrate (1.22 g) and 2-[3-[(3-hydroxymethyl)phenoxy]propyl]-1H-isoindole-1,3(2H)-dione (3.8 g) in ethanol (50 ml) was refluxed for 5 hours. The suspension was filtered and the filtrate evaporated to dryness to give a residue which was distilled (155°/0.06 mm). The solid which formed was crystallised from cyclohexane to give the title compound (1.25 g) m.p. 69°–71°.

C.

N-[2-[[5-[(Dimethylamino)methyl]-2-furanylmethyl]thio]ethyl]-N'-[3-[3-(hydroxymethyl)phenoxy]propyl]-2-nitro-1,1-ethenediamine A solution of N,N-dimethyl-5-[[[2-[(1-methylthio-2-nitro-ethenyl)amino]ethyl]thio]methyl]-2-furanmethanamine (0.91 g) and 3-[(3-hydroxymethyl)phenoxy]propanamine (0.5 g) in dry tetrahydrofuran (25 ml) was refluxed for 5 mins. The solution was evaporated to dryness and the residue heated at 100° for 1 hr. The oily product was chromatographed (silica/methanol) and the appropriate eluate evaporated to dryness to give the title compound as the bicarbonate hydrate as a brown gum (1.05 g).

TLC (silica/methanol) RF 0.31.

NMR $(CDCl_3)\tau$: 7.90 m, 7.80 s (8H); 7.35 brt (2H); 6.63 s+br (6H); 6.35 s (2H); 6.00 t+br (3H); 5.38 s (2H); 3.88 s (2H); 3.50 s (1H); 3.0–3.3 m (4H); 2.8 dd (1H); −0.4 br (1H).

EXAMPLE 6

N-[3-[5-[(Dimethylamino)methyl]-2-furanylmethoxy]propyl]-2-nitro-N'-[2-[(3-pyridinylmethyl)thio]ethyl]-1,1-ethenediamine

A.

5-[(3-Aminopropoxy)methyl]-N,N-dimethyl-2-furanmethanamine

To a stirred solution of methanesulphonic acid (18 ml) in dry tetrahydrofuran (40 ml) kept at room temperature was added, with stirring, a mixture of 5-[(dimethylamino)methyl]-2-furanmethanol (4.65 g) and 3-amino-1-propanol (6.75 g). After 3 days the suspension was heated on a steam bath for 30 mins. Excess anhydrous sodium carbonate and ethyl acetate (100 ml) were added and the heating continued for 20 mins. The hot suspension was filtered and the residue washed with hot ethyl acetate (3×50 ml). The combined filtrates were evaporated to dryness, water (150 ml) added and the solution extracted with ethyl acetate (3×50 ml). The aqueous fraction was acidified with oxalic acid (5 g) and the solution evaporated to low bulk. Ethyl acetate (100 ml) and excess anhydrous sodium carbonate were added and the suspension heated to boiling point for 30 mins. The hot suspension was filtered and the combined filtrates and washings evaporated to dryness. The oily residue was distilled (100°–110°/0.2 mm) to give the title compound (2.76 g).

TLC (silica/methanol-0.88 ammonia 19:1) Rf 0.3

B.

N,N-Dimethyl-5-[[3-[(1-methylthio-2-nitroethenyl)amino]propoxy]methyl]-2-furanmethanamine To a stirred solution of 1,1-bis(methylthio)-2-nitroethene (3.96 g) in dry dioxan (25 ml) at 70° was added dropwise 5-[(3-aminopropoxy)methyl]-N,N-dimethyl-2-furanmethanamine (1.27 g). After 1 hr the reaction was allowed to cool and the solid which separated was filtered. The filtrate and washings were combined and evaporated to dryness, a solution of succinic acid (1 g) in water (25 ml) added to the residue and the suspension filtered. The filtrate was washed with ethyl acetate (2×40 ml) then evaporated to 10 ml. The solution was basified with sodium carbonate and the oily precipitate which separated was extracted into ethyl acetate (3×25 ml). The combined extracts were dried (anhyd. sodium carbonate), the suspension filtered and evaporated to dryness to yield the title compound (1.34 g) as a brown oil.

TLC (silica/methanol) Rf 0.45.

C.

N-[3-[5-[(Dimethylamino)methyl]-2-furanylmethoxy]-propyl]-2-nitro-N'-[2-[(3-pyridinylmethyl)thio]ethyl]-1,1-ethenediamine A mixture of N,N-dimethyl-5-[[3-[(1-methylthio-2-nitroethenyl)amino]propoxy]methyl]-2-furanmethanamine (0.7 g) and 2-[(3-pyridinylmethyl)thio]ethanamine (0.36 g) was heated at 98°-100° for 3 hr. The oily residue was chromatographed (silica/methanol-0.88 ammonia 79:1) and the appropriate eluate evaporated to dryness to give the title compound as a hemihydrate as an oil (0.52 g).

TLC (silica/methanol-0.88 ammonia 79:1) Rf 0.45.
Found: C, 55.2; H, 7.1; N, 14.9. $C_{21}H_{31}N_5O_4S.\frac{1}{2}H_2O$ requires: C, 55.0; H, 7.0; N, 15.3%.

EXAMPLE 7

N-[2-[[5-[(Dimethylamino)methyl]-2-furanylmethyl]thio]ethyl]-2-nitro-N'-[2-[[2-(2-pyridinyl)ethyl]thio]ethyl]-1,1-ethenediamine

A. 2-[[2-(2-Pyridinyl)ethyl]thio]ethanamine dihydrochloride

To a solution of sodium (9.2 g) in ethanol (300 ml) at 5° was added 2-aminoethanethiol hydrochloride (24 g). The solution was stirred at 5°-10° for 1.5 hr, 2-ethenylpyridine (20 g) was added and the mixture refluxed for 16 hr. The cooled mixture was filtered, the filtrate evaporated to dryness and the residue extracted with ether. Excess ethereal hydrogen chloride was added and the gummy precipitate crystallised from methanol-isopropanol to give the title compound (12.5 g) m.p. 151°-154°.

B.

N-[2-[[5-(Dimethylamino)methyl]-2-furanylmethyl]thio]ethyl]-2-nitro-N'-[2-[[2-(2-pyridinyl)ethyl]thiol]ethyl]-1,1-ethenediamine A mixture of N,N-dimethyl-5-[[[2-[(1-methylthio-2-nitroethenyl)amino]ethyl]thio]methyl]-2-furanmethanamine (1 g) and 2-[[2-(2-pyridinyl)ethyl]thio]ethanamine (0.6 g) (obtained from the dihydrochloride salt) was heated at 100° for 3 hr. The oily residue was chromatographed (silica/methanol) and the appropriate eluate evaporated to dryness to give the title compound as an amber oil (1.05 g).

TLC (silica/methanol-0.88 ammonia 79:1) Rf 0.38.
Found: C, 54.1; H, 6.8; N, 15.0. $C_{21}H_{31}N_5O_3S_2$ requires: C, 54.2; H, 6.7; N, 15.0%.

EXAMPLE 8

N-[2-[[5-[(Dimethylamino)methyl]-2-furanylmethyl]thio]ethyl]-N'-[[(2-furanylmethyl)thio]ethyl]-N''-methylsulphonylguanidine

A.

N-[2-[[5-[(Dimethylamino)methyl]-2-furanylmethyl]thio]ethyl]-N'-methylsulphonylcarbamimidothioic acid, methyl ester A mixture of 5-[[(2-aminoethyl)thio]methyl]-N,N-dimethyl-furanmethanamine (2.97 g) and methylsulphonylcarbonimidodithioic acid, dimethyl ester (4.0 g) in ethyl acetate (250 ml) was refluxed for 18 hours. The mixture was washed with acetic acid (0.126 ml) in water (20 ml) three times, the aqueous extracts combined and the pH adjusted to 9 with 8% aqueous potassium carbonate. The oily suspension was extracted with ethyl acetate (3×125 ml), the combined extracts dried (magnesium sulphate) and evaporated to dryness to give the title compound (4 g) as a yellow oil.

Found: C, 42.9; H, 6.6; N, 11.3. $C_{13}H_{23}N_3O_3S_3$ requires: C, 42.6; H, 6.3; N, 11.5%.

B.

N-[2-[[5-[(Dimethylamino)methyl]-2-furanylmethyl]thio]ethyl]-N'-[[(2-furanylmethyl)thio]ethyl]-N''-methylsulphonylguanidine A mixture of N-[2-[[5-[(dimethylamino)methyl]-2-furanylmethyl]thio]ethyl]-N'-methylsulphonylcarbamimidothioic acid, methyl ester (1.82 g) and [2-(2-furanylmethyl)thio]ethanamine (0.785 g) was heated at 120° for 5 hours. The reaction mixture was chromatographed (silica/ethyl acetate-methanol 3:1) and the appropriate eluate evaporated to dryness to give the title compound (2.18 g), as a yellow oil.

TLC (silica/methanol-0.88 ammonia 79:1) Rf 0.49.
Found: C, 47.9; H, 6.5; N, 11.6. $C_{19}H_{30}N_4O_4S_3$ requires: C, 48.1; H, 6.4; N, 11.8%.

EXAMPLE 9

(i)

N,N'-bis-[2-[[5-[(Dimethylamino)methyl]-2-furanylmethyl]thio]ethyl]-2-nitro-1,1-ethenediamine A mixture of 1,1-bis(methylthio)-2-nitroethene (1.65 g) and 5-[[(2-aminoethyl)thio]methyl]-N,N-dimethyl-2-furanmethanamine (4.5 g) was heated at 98°-100° for 1 hour. The oily residue was triturated with ether to give the title compound (4.4 g) m.p. 58°-62°.

Similarly prepared was:

(ii) N,N'-bis-[2-[[5-[[(1-Methylethyl)amino]methyl]-2-furanylmethyl]thio]ethyl]-2-nitro-1,1-ethenediamine
from 5-[[(2-aminoethyl)thio]methyl]-N-(1-methylethyl)-2-furanmethanamine (1.1 g) and 1,1-bis-(methylthio)-2-nitroethene (0.36 g) at 98°-100° for 1 hr, the crude product being purified as the bis-oxalate salt (1 g) m.p. 114°-115°. The free base was liberated from the bis-oxalate salt with 8% aqueous sodium bicarbonate and extracted with ethyl acetate. The dried extracts (magnesium sulphate) were evaporated to give the title compound (0.62 g) as a hydrate as an oil.

TLC (silica/methanol-0.88 ammonia 79:1) Rf 0.44.
NMR (D$_2$O): 8.62 d (12H); 7.12 tr (4H); 6.5 m (6H); 6.12 s (4H); 5.70 s (4H); 3.60 (2H), 3.38 (2H) AB.

EXAMPLE 10

N,N'-bis[2-[[5-[(Methylamino)methyl]-2-furanylmethyl]thio]ethyl]-2-nitro-1,1-ethenediamine A mixture of 1,1-bis(methylthio)-2-nitroethene (0.825 g) and 5-[[(2-aminoethyl)thio]methyl]-N,N-dimethyl 2-furanmethanamine (2 g) was heated at 100° for 2 hours. The oily product was subjected to column chromatography (Silica/0.2% ammoniacal methanol) to give the title compound as an orange-brown gum (0.9 g), NMR (CDCl$_3$) 7.60 s (6H); 7.25 m (4H); 6.7 m (4H); 6.3 s (8H); 3.85 s (4H); 3.40 s (1H).

EXAMPLE 11

1,3-bis[2-[[5-[(Dimethylamino)methyl]-2-furanylmethyl]thio]ethyl]urea

A mixture of carbonyldiimidazole (2.27 g) and 5-[[(2-aminoethyl)thio]methyl]-N,N-dimethyl-2-furanmethanamine (6.0 g) was heated under reflux in dry tetrahydrofuran (75 ml) for 5 hours. The solvent was evaporated and the oil obtained heated on a steam bath in vacuo. Trituration of the residue with cold diethyl ether gave a solid which crystallised from ice-cold ether as white prisms (5.8 g) m.p. 68°–69.5°.

EXAMPLE 12

(i)
N''-Cyano-N,N'-bis[2-[[5-[(dimethylamino)methyl]-2-furanylmethyl]thio]ethyl]guanidine A mixture of 5-[[(2-aminoethyl)thio]methyl]N,N-dimethyl-2-furanmethanamine (1.39 g) and N'-cyano-N-[2-[[5-[(dimethylamino)methyl]-2-furanylmethyl]thio]ethyl]carbamimidothioic acid, methyl ester (2.0 g) was heated at 120° for 2 days. The oily product was subjected to column chromatography (silica-methanol) giving the title compound as a yellow oil (1.75 g).

Found: C, 55.0; H, 7.4; N, 17.6. C$_{22}$H$_{36}$N$_6$O$_2$S$_2$ requires: C, 55.4; H, 7.2; N, 17.6.

Similarly prepared were:

(ii) N,N'-bis-[2-[[5-[(Dimethylamino)methyl]-2-furanylmethyl]thio]ethyl]-N''-methylsulphonylguanidine (1.5 g) from N-[2-[[5-[(dimethylamino)methyl]-2-furanylmethyl]thio]ethyl]-N'-methylsulphonylcarbamimidothioic acid, methyl ester (1.5 g) and 5-[[(2-aminoethyl)thio]methyl]-N,N-dimethyl-2-furanmethanamine (0.88 g) at 120° for 5 hr.

TLC (silica/methanol-0.88 ammonia 79:1) Rf 0.43.
Found: C, 49.3; H, 7.1; N, 12.9.
C$_{22}$H$_{37}$N$_5$O$_4$S$_3$ requires: C, 49.7; H, 7.0; N, 13.2%.

(iii) N-[2-[[5-[(Dimethylamino)methyl]-2-furanylmethyl]thio]ethyl]-N'-[3-[3-[(dimethylamino)methyl]phenoxy]propyl]-2-nitro-1,1-ethenediamine (1.24 g) from N,N-dimethyl-5-[[[2-[(1-methylthio-2-nitroethenyl)amino]ethyl]thio]methyl]-2-furanmethanamine (1.5 g) and 3-(3-aminopropoxy)-N,N-dimethylbenzenemethanamine (0.94 g) at 98°–100° for 4 hours.

TLC (silica/methanol-0.88 ammonia 79:1) Rf 0.28.
Found: C, 58.3; H, 7.8; N, 14.1. C$_{24}$H$_{37}$N$_5$O$_4$S requires: C, 58.6; H, 7.6; N, 14.3%.

(iv) N-[2-[[5-[(Dimethylamino)methyl]-2-furanylmethyl]thio]ethyl]-N'-[2-[[5-[(dimethylamino)methyl]-2-thienylmethyl]thio]ethyl]-2-nitro-1,1-ethenediamine (0.97 g) from N,N-dimethyl-5-[[[2-[(1-methylthio-2-nitroethenyl)amino]ethyl]thio]methyl]-2-furanmethanamine (0.99 g) and 5-[[(2-aminoethyl)thio]methyl]-N,N-dimethyl-2-thiophenemethanamine (0.74 g) at 98°–100° for 6 hours.

TLC (silica/methanol-0.88 ammonia 79:1) Rf 0.3.
Found: C, 51.2; H, 7.0; N, 13.6. C$_{22}$H$_{35}$N$_5$O$_3$S$_3$ requires: C, 51.4; H, 6.9; N, 13.6%.

(v) N-[2-[[5-[(Dimethylamino)methyl]-2-furanylmethyl]thio]ethyl]-N'-[3-[3-[(dimethylamino)methyl]phenoxy]propyl]-N''-methylsulphonylguanidine (0.89 g) as a hydrate from N-[2-[[5-[(dimethylamino)methyl]-2-furanylmethyl]thio]ethyl]-N'-methylsulphonylcarbamimidothioic acid, methyl ester (1 g) and 3-(3-aminopropoxy)-N,N-dimethylbenzenemethanamine (0.57 g) at 98°–100° for 4 hours.

TLC (silica/methanol-0.88 ammonia 79:1) Rf 0.43.
NMR (CDCl$_3$) τ: 7.95 m (2H); 7.78 s (12H); 7.40 tr (2H); 7.10 s (3H); 6.5–6.8 s+m (8H); 6.34 s (2H); 5.95 tr (2H); 3.85 AB+br (3H); 3.0–3.3 m (4H); 2.75 m (1H).

(vi) N''-Cyano-N-[2-[[5-[(Dimethylamino)methyl]-2-furanylmethyl]thio]ethyl]-N'-[3-[3-[(dimethylamino)methyl]phenoxy]propyl]guanidine (0.99 g) as a hydrate from N'-cyano-N-[2-[[5-[(dimethylamino)methyl]-2-furanyl-methyl]thio]ethyl]carbamimidothioic acid, methyl ester (1.56 g) and 3-(3-aminopropoxy)-N,N-dimethylbenzenemethanamine (1.04 g) at 98°–100° for 18.5 hours.

TLC (silica/methanol-0.88 ammonia 79:1) Rf 0.45.
Found: C, 59.9; H, 7.9; N, 17.2; S, 6.8. C$_{24}$H$_{36}$N$_6$O$_2$S·½H$_2$O requires: C, 59.8; H, 7.7; N, 17.5; S, 6.7%.

(vii) N-[3-[5-[(Dimethylamino)methyl]-2-furanylmethoxy]propyl]-N'-[2-[[5-[(dimethylamino)methyl]-2-furanylmethyl]thio]ethyl-2-nitro-1,1-ethenediamine (1.10 g) from N,N-dimethyl-5-[[[2-[(1-methylthio-2-nitroethenyl)amino]ethyl]thio]methyl]-2-furanmethanamine (1.66 g) and 5-[(3-aminopropoxy)methyl]-N,N-dimethyl-2-furanmethanamine (1.06 g) at 98°–100° for 3 hours.

TLC (silica/methanol-0.88 ammonia 79:1) Rf 0.4.
NMR (CDCl$_3$)τ: 8.1 m (2H); 7.75 s (12H); 7.3 tr (2H); 6.2–7 m, 6.58 s, 6.28 s (14H); 5.54 s (2H); 3.84 s, 3.7 AB (4H); 3.44 s (1H).

(viii) N''-Cyano-N-[2-[[5-[(dimethylamino)methyl]-2-furanylmethyl]thio]ethyl]-N'-[2-[[5-[(methylamino)methyl]-2-furanylmethyl]thio]ethyl]guanidine (1.23 g) as a hydrate from N'-cyano-N-[2-[[5-[(dimethylamino)methyl]-2-furanylmethyl]thio]ethyl]carbamimidothioic acid, methyl ester (1.0 g) and 5-[[(2-aminoethyl)thio]methyl]-N-methyl-2-furanmethanamine (0.71 g) at 98°–100° for 4 hours.

TLC (silica/methanol-0.88 ammonia 79:1) Rf 0.4.
NMR (CDCl$_3$)τ: 7.8 m 7.73 s (7H); 7.58 s (3H); 7.28 tr (4H); 6.70 m 6.57 s (6H); 6.28 s, 6.27 s (6H); 3.4–4.3 brm, 3.86 s (6H).

(ix) N-[2-[[5-[(Dimethylamino)methyl]-2-furanylmethyl]thio]ethyl]-N'-[2-[[5-[(methylamino)methyl]-2-furanylmethyl]thio]ethyl]-2-nitro-1,1-ethenediamine (0.47 g) as a hydrate from N,N-dimethyl-5-[[[2-[(1-methylthio-2-nitroethenyl)amino]ethyl]thio]methyl]-2-furanmethanamine (0.55 g) and 5-[[(2-aminoethyl)thio]methyl]-N-methyl-2-furanmethanamine (0.33 g) at 98°–100° C. for 1.25 hours.

TLC (silica/methanol-0.88 ammonia 79:1) Rf 0.3.
NMR (CDCl$_3$)τ: 7.9 br (1H); 7.78 s (6H); 7.59 s (3H); 7.26 tr (4H); 6.70 br, 6.60 s (6H); 6.42 s, 6.40 s (6H); 3.90 AB (4H); 3.50 s (1H); −0.5 br (1H).

(x) N-[3-[5-[(Dimethylamino)methyl]-2-furanylmethoxy]propyl]-N'-[3-[3-[(dimethylamino)methyl]phenoxy]propyl]-2-nitro-1,1-ethenediamine (0.5 g) as a hydrate from N,N-dimethyl-3-[3-[(1-methylthio-2- nitro-ethenyl) amino]propoxy]benzenemethanamine (1.0 g) and 5-[(3-aminopropoxy)methyl]N,N-dimethyl-2-furanmethanamine (0.7 g) at 98°-100° for 18 hours.

TLC (silica/methanol-0.88 ammonia 79:1) Rf 0.33.

NMR (CDCl$_3$)τ: 8.0-8.4 m, 7.80 s (16H); 6.3-7.0 m, 6.42 tr (10H); 5.98 tr (2H); 5.60 s (2H); 3.7-3.9 AB+br (3H); 3.45 s, 3.0-3.3 m, 2.8 m (5H).

(xi) N-[2-[[5-[(Dimethylamino)methyl]-2-furanylmethyl]thio]ethyl]-N'-[2-[[5-[[hydroxy(methyl)amino]methyl]-2-furanylmethyl]thio]ethyl]-2-nitro-1,1-ethenediamine (0.81 g) from N,N-dimethyl-5-[[[2-[(1-methylthio-2-nitroethenyl)amino]ethyl]thio]methyl]-2-furanmethanamine (2.0 g) and 5-[[(2-aminoethyl)thio]methyl]-N-hydroxy-N-methyl-2-furanmethanamine (1.3 g) at 98°-100° for 6 hours.

TLC (silica/methanol-0.88 ammonia 79:1) Rf 0.39.

Found: C,50.5; H,6.7; N,13.7. C$_{21}$H$_{33}$N$_5$O$_5$S$_2$ requires: C,50.5; H,6.7; N,14.0%.

(xii) N-[2-[[5-[(Dimethylamino)methyl]-2-furanylmethyl]thio]ethyl]-2-nitro-N'-[2-[[5-[(1-pyrrolidinyl)methyl]-2-furanylmethyl]thio]ethyl]-1,1-ethenediamine (1.53 g) as a hydrate from N,N-dimethyl-5-[[[2-[(1-methylthio-2-nitroethenyl)amino]ethyl]thio]methyl]-2-furanmethanamine (1.38 g) and 2-[[5-[(1-pyrrolidinyl)methyl]-2-furanylmethyl]thio]ethanamine (1 g) at 98°-100° for 3 hours.

TLC (silica/methanol-0.88 ammonia 79:1) Rf 0.4.

NMR (CDCl$_3$)τ: 8.24 m (4H); 7.78 s (6H); 7.48 m (4H); 7.22 tr (4H); 6.65 br, 6.58 s (6H); 6.40 s (2H); 6.27 s (4H); 3.85 2×AB (4H); 3.45 br+s (2H); −0.5 br (1H).

(xxi) N"-Cyano-N-[3-3-[(dimethylamino)methyl]phenoxy]propyl]-N-'-[2-[[5-[(1-pyrrolidinyl)methyl]-2-furanylmethyl]thio]ethyl]guanidine (0.3 g) as a hydrate from N'-cyano-N-[3-[3-[(dimethylamino)methyl]phenoxy]propyl]carbaminidothioic acid, methyl ester (0.75 g) and 2-[[5-[(1-pyrrolidinyl)methyl]-2-furanylmethyl]thio]ethanamine (0.65 g) at 98°-100° for 3 hours.

TLC (silica/methanol-0.88 ammonia 79:1) Rf 0.42.

NMR (CDCl$_3$)τ: 8.1-8.4 m (4H); 8.0 s, 7.78 s (8H); 7.3-7.6 m (6H); 6.6-6.9 m, 6.65 s, 6.46 s, 6.35 s (10H); 5.95 tr (2H); 4.30 tr (1H); 4.05 tr, 3.90 s (3H); 3.0-3.3 m (3H); 2.80 tr (1H).

(xiv) N"-Cyano-N-[2-[[5-[(dimethylamino)methyl]-2-furanylmethyl]thio]ethyl]-N'-[3-[3-[(1-pyrrolidinyl) methyl]phenoxy]propyl]guanidine (0.75 g) as a hydrate from N'-cyano-N-[2-[[5-[(dimethylamino)methyl]-2-furanylmethyl]thio]ethyl]carbamimidothioic acid, methyl ester (1.0 g) and 3-[3-[(1-pyrrolidinyl)methyl]phenoxy]propanamine (0.83 g) at 100° for 2 hours.

TLC (silica/methanol-0.88 ammonia 79:1) Rf 0.41.

NMR (CDCl$_3$)τ: 8.25 m, 7.98 m, 7.78 s (12H); 7.3-7.7 m (6H); 6.4-7.0 m, 6.62 s, 6.42 s, 6.38 s (10H); 5.98 tr (2H); 4.27 tr, 4.02 tr, 3.9 s (4H); 3.0-3.3 m (3H); 2.8 tr (1H).

(xv) N-[3-[3-[(Dimethylamino)methyl]phenoxy]propyl]-2-nitro-N'-[2-[[5-[(1-pyrrolidinyl)methyl]-2-thiophenylmethyl]thio]ethyl]-1,1-ethenediamine (0.33 g) as a hydrate from N,N-dimethyl-3-[3-[(1-methylthio-2-nitroethenyl)amino]propoxy]benzenemethanamine (1.0 g) and 2-[[5-[(1-pyrrolidinyl)methyl]-2-thiophenylmethyl]thio]ethanamine (0.33 g) at 100° for 5 hours.

TLC (silica/methanol-0.88 ammonia 79:1) Rf 0.25.

NMR (CDCl$_3$)τ: 8.25 m (4H); 7.9 m, 7.8 s (8H); 7.2-7.7 m (6H); 6.4-7.0 br, 6.63 s (6H); 6.28 s (2H); 6.18 s (2H); 5.95 tr (2H); 3.5-4.5 br (1H); 3.0-3.5 m (2H); 2.78 tr (1H); −0.5 br (1H).

(xvi) N-[2-[[5-[(Dimethylamino)methyl]-2-furanylmethyl]thio]ethyl]-2-nitro-N'-[2-[[5-[(1-pyrrolidinyl)methyl]-2-thiophenylmethyl]thio]ethyl]-1,1-ethenediamine (1.03 g) as a hydrate from N,N-dimethyl-5-[[[2-[(1-methylthio-2-nitroethenyl)amino]ethyl9 thio]methyl]-2-furanmethanamine (1.0 g) and 2-[[5-[(1-pyrrolidinyl)methyl]-2-thiophenylmethyl]thio]ethanamine (0.85 g) at 98°-100° for 4 hours.

TLC (silica/methanol-0.88 ammonia 79:1) Rf 0.34.

NMR (CDCl$_3$)τ: 8.28 m (4H); 7.80 s (6H); 7.52 m, 7.30 tr (8H); 6.70 br, 6.64 s (6H); 6.30 s (4H); 6.20 s (2H); 3.95 AB (2H); 3.52 s+br (2H); 3.30 AB (2H); −0.5 br (1H).

(xvii) N-[2-[[5-[(Dimethylamino)methyl]-2-furanylmethyl]thio]ethyl]-2-nitro-N'-[3-[3-[(1-pyrrolidinyl)methyl]phenoxy]propyl]-1,1-ethenediamine (0.7 g) from N,N-dimethyl-5-[[[2-[(1-methylthio-2-nitroethenyl)amino]ethyl]thio]methyl]-2-furanmethanamine (1.0 g) and 3-[3-[(1-pyrrolidinyl)methyl]phenoxy]propanamine (0.77 g) at 100° for 4 hours.

TLC (silica/methanol-0.88 ammonia 79:1) Rf 0.21.

NMR (CDCl$_3$)τ: 8.22 m(4H); 7.90 m, 7.77 s (8H); 7.52 m, 7.32 tr (6H); 6.4-7.0 br, 6.60 s (6H); 6.45 s (2H); 6.32 s (2H); 5.98 tr (2H); 3.88 s (2H); 3.45 s (1H); 3.0-3.3 m (3H); 2.78 tr (1H); −0.5 br (1H).

(xviii) N"-Cyano-N-[3-[5-[(dimethylamino)methyl]-2-furanylmethoxy]propyl]-N'-[3-[3-[(dimethylamino) methyl]phenoxy]propyl]guanidine (0.48 g) as a hydrate from N'-cyano-N-[3-[3-[(dimethylamino)methyl]phenoxy]propyl]carbamimidothioic acid, methyl ester (1.0 g) and 5-[(3-aminopropoxy)methyl]-N,N-dimethyl-2-furanmethanamine (0.76 g) at 100° for 4 hours.

TLC (silica/methanol-0.88 ammonia 79:1) Rf 0.34.

Found: C,61.8; H,8.0; N,17.0. C$_{25}$H$_{38}$N$_6$O$_3$.H$_2$O requires: C,61.5; H,8.3; N,17.2%.

(xix) N"-Cyano-N-[3-[5-[(dimethylamino)methyl]-2-furanylmethoxy]propyl]-N'-[2-[[5-[(dimethylamino) methyl]-2-furanylmethyl]thio]ethyl]guanidine (0.81 g) as a hydrate from N'-cyano-N-[2-[[5-[(dimethylamino) methyl]-2-furanylmethyl]thio]ethyl]carbamimidothioic acid, methyl ester (1.0 g) and 5-[(3-aminopropoxy) methyl]-N,N-dimethyl-2-furanmethanamine (0.75 g) at 100° for 4 hours.

TLC (silica/methanol-0.88 ammonia 79:1) Rf 0.43.

NMR (CDCl$_3$)τ: 8.2 m (2H); 7.74 s (12H); 7.38 tr (2H); 6.71 q, 6.56 s (8H); 6.40 tr (2H); 6.30 s (2H); 5.57 s (2H); 4.06 2xtr (2H); 3.7-3.9 2AB (4H).

(xx) N"-Cyano-N-[2-[[5-[(dimethylamino)methyl]-2-furanylmethyl]thio]ethyl]-N'-[2-[[5-[(methylamino) methyl]-2-furanylmethyl]thio]ethyl]guanidine (1.23 g) as a hydrate from N'-cyano-N-[2-[[5-[(dimethylamino) methyl]-2-furanylmethyl]thio]ethyl]carbamimidothioic acid, methyl ester (1.0 g) and 5-[[(2-aminoethyl) thio]methyl]-N,N-dimethyl-2-furanmethanamine (0.71 g) at 98°-100° for 4 hours. TLC (silica/methanol-0.88 ammonia 79:1) Rf 0.4. NMR (CDCl$_3$)τ: 7.8 m, 7.73 s (7H); 7.58 s (3H); 7.28 tr (4H); 6.70 m, 6.57 s (6H); 6.28 s, 6.27 s (6H); 3.4-4.3 br m, 3.86 s (6H).

EXAMPLE 13

(i)

N,N'-bis-[3-[3-[(Dimethylamino)methyl]phenoxy]-propyl]-2-nitro-1,1-ethenediamine 3-(3-aminopropoxy)-N,N-dimethylbenzenemethanamine (1.09 g) and 1,1-bis(methylthio)-2-nitroethene (413 mg) were heated as an intimate mixture on a steam bath for 90 minutes. The resulting oil was washed with ether and purified by column chromatography on silica using 2% 0.88 ammonia in methanol to give the title compound as a pale yellow oil (0.74 g). Rf 0.30, silica/2% 0.88 ammonia in methanol.

Similarly prepared were:

(ii) 2-Nitro-N,N'-bis-[2-[[5-[(1-pyrrolidinyl)methyl]-2-furanylmethyl]thio]ethyl]-1,1-ethenediamine (0.54 g) as a hydrate from 1,1-bis(methylthio)-2-nitroethene (0.21 g) and 2-[[5-[(1-pyrrolidinyl)methyl]-2-furanylmethyl]thio]ethanamine (0.66 g) at 98°–100° for 2 hr.

TLC (silica/methanol-0.88 ammonia 79:1) Rf 0.24.

NMR (CDCl$_3$)$\tau$: 8.0–8.4 m (8H); 7.0–7.7 m (12H); 6.7 m (4H); 6.38 s 6.29 s (8H); 3.86 s (4H); 3.48 s (1H).

(iii) N,N'-bis[3-5-[(Dimethylamino)methyl]-2-furanylmethoxy]propyl]-2-nitro-1,1-ethenediamine (0.83 g) as a hydrate from 5-[(3-aminopropoxy)methyl]-N,N-dimethyl-2-furanmethanamine (1.4 g) and 1,1-bis(methylthio)-2-nitroethane (0.54 g) at 98°–100° for 4 hr.

TLC (silica/methanol-0.88 ammonia 79:1) Rf 0.43.

NMR (CDCl$_3$)$\tau$: 8.2 m (4H); 7.80 s (12H); 6.82 q (4H); 6.61 s, 6.48 m (8H); 5.61 s (4H); 3.7–4.0 AB and br (5H); 3.48 s (1H); −0.3 br (1H).

(iv) N,N'-bis-[2-[[5-[(Dimethylamino)methyl]-2-thiophenylmethyl]thio]ethyl]-2-nitro-1,1-ethenediamine (0.56 g) from 5-[[(2-aminoethyl)thio]methyl]-N,N-dimethyl-2-thiophenemethanamine (0.9 g) and 1,1-bis-(methylthio)-2-nitroethene (0.31 g) at 98°–100° for 10 hr.

TLC (silica/methanol-0.88 ammonia 79:1) Rf 0.52.

Found: C,49.8; H,6.5; N,13.1. C$_{22}$H$_{35}$N$_5$O$_2$S$_4$ requires: C,49.9; H,6.7; H,13.2%.

(v) N''-Cyano-N,N'-bis[3-3-[(dimethylamino)methyl]phenoxy]propyl]guanidine (1.1 g) as a hydrate from 3-(3-aminopropoxy)-N,N-dimethylbenzenemethanamine (1.71 g) and cyanocarbonimidodithioic acid, dimethyl ester (0.6 g) at 98°–100° for 16 hr.

TLC (silica/methanol-0.88 ammonia 79:1) Rf 0.33.

NMR (CDCl$_3$)$\tau$: 8.0 m, 7.80 s (16H); 6.63 m and s (8H); 5.99 tr (4H); 4.18 tr (2H); 3–3.4 m (6H); 2.79 m (2H).

(vi) N''-Cyano-N,N'-bis-[2-[[5-[(1-pyrrolidinyl)methyl]-2-furanylmethyl]thio]ethyl]guanidine (0.53 g) as a hydrate from 2-[[5-[(1-pyrrolidinyl)methyl]-2-furanylmethyl]thio]ethanamine (1.5 g) and cyanocarbonimidodithioic acid, dimethyl ester (0.45 g) as 98°–100° for 8 hr.

TLC (silica/methanol-0.88 ammonia 79:1) Rf 0.39.

NMR (CDCl$_3$)$\tau$: 8.22 m (8H); 7.48 m, 7.30 tr (12H); 6.70 q (4H); 6.41 s (4H); 6.28 s (4H); 4.07 tr (2H); 3.9 AB (4H).

(vii) 2-Nitro-N,N'-bis-[3-3-[(1-pyrrolidinyl)methyl]phenoxy]propyl]-1,1-ethenediamine (0.9 g) as a hydrate from 3-[3-(1-pyrrolidinylmethyl)phenoxy]propanamine (2.34 g) and 1,1-bis-(methylthio)-2-nitroethane (0.82 g) at 100° for 3 hr.

TLC (silica/methanol-0.88 ammonia 20:1) Rf 0.38.

NMR (CDCl$_3$)$\tau$: 8.28 m, 7.99 br m (12H); 7.55 m (8H); 6.68 brm, 6.48 s (8H); 6.00 tr (4H); 3.43 s (1H); 3–3.4 m (6H); 2.85 m (2H); 3.84 brs (1H); −0.40 brs (1H).

(viii) N''-Cyano-N,N'-bis-[3-[5-[(dimethylamino) methyl]-2-furanylmethoxy]propyl]guanidine (0.66 g) as a hydrate from 5-[(3-aminopropoxy)methyl]-N,N-dimethyl-2-furanmethanamine (1.5 g) and cyanocarbonimidodithioic acid, dimethyl ester (0.45 g) at 98°–100° for 6 hr.

TLC (silica/methanol-0.88 ammonia 79:1) Rf 0.43.

NMR (CDCl$_3$)$\tau$: 8.28 m (4H); 7.80 s (12H); 6.82 q (4H); 6.60 s (4H); 6.50 tr (4H); 5.62 s (4H); 4.20 brt (2H); 3.91 (2H); 3.80 AB (2H).

EXAMPLE 14

2-Nitro-N,N'-bis-[2-[[5-[[(2,2,2-trifluoroethyl)amino]methyl]-2-furanylmethyl]thio]ethyl]-1,1-ethenediamine

A.

5-[[(2-Aminoethyl)thio]methyl]-N-(2,2,2-trifluoroethyl)-2-furanmethanamine

Aqueous formaldehyde (37%, 2.8 ml) was slowly added to a mixture of 2-furanmethanol (3.05 g) and 2,2,2-trifluoroethanamine hydrochloride (4.55 g) cooled in ice. The mixture was kept at room temperature for 18 hr, ethyl acetate (200 ml) and excess anhydrous sodium carbonate were added and after 3 hr the suspension was filtered. The filtrate was treated with charcoal, filtered and evaporated to give a brown oil (5.53 g). To a solution of this in 2 N hydrochloric acid (10 ml) at 0° was slowly added a solution of 2-aminoethanethiol hydrochloride (3 g) in concentrated hydrochloric acid (15 ml). The solution was kept at 0° for 16 hr and at room temperature for 24 hr. To the solution was added excess anhydrous sodium carbonate and the solid residue extracted with isopropanol. Evaporation of the extract gave a brown oil which was chromatographed (silica/methanol-0.88 ammonia 79:1). The appropriate eluate was evaporated to dryness to give the title compound (3.3 g) as an oil.

TLC (silica/methanol-0.88 ammonia 79:1) Rf 0.48.

B. 2-Nitro-N,N'-bis-[2-[[5-[(2,2,2-trifluoroethyl) amino]methyl]-2-furanylmethyl]thio]ethyl]-1,1-ethenediamine A mixture of 5-[[(2-aminoethyl)thio]methyl]-N-(2,2,2-trifluoroethyl)-2-furanmethanamine (0.83 g) and 1,1-bis-(methylthio)-2-nitroethene (0.25 g) was heated at 98°–100° for 3 hr. The gummy residue was chromatographed (silica/ethyl acetate then ethyl acetate/ethanol 9:1) and the appropriate eluate evaporated to dryness to give the title compound (0.2 g) as an oil.

TLC (silica/ethyl acetate) Rf 0.39.

Found: C,44.1; H,4.9; N,11.2. C$_{22}$H$_{29}$F$_6$N$_5$O$_4$S$_2$ requires: C,43.6; H,4.8; N,11.6%.

EXAMPLE 15

N,N'-bis-[2-[[5-[(Cyclopropylamino)methyl]-2-furanylmethyl]thio]ethyl]-2-nitro-1,1-ethenediamine A. 5-[(Cyclopropylamino)methyl]-2-furanmethanol, oxalate salt Aqueous formaldehyde (36%, 15 ml) was added slowly to a cooled mixture of cyclopropylamine hydrochloride (16 g) and 2-furanmethanol (15 g). After 2 days at room temperature the solution was basified and dried with anhydrous sodium carbonate. The solid was extracted with isopropanol and the solvent evaporated to give an oil which was chromatographed (silica/ethyl acetate-ethanol 9:1). The appropriate eluate was evaporated to dryness and a solution of the oily residue in ethanol was acidified with a solution of oxalic acid in ethanol to give the title compound (11.17 g) as a crystalline solid.

TLC (silica/ethyl acetate-ethanol 9:1) Rf 0.4.

B.

5-[[2-Aminoethyl)thio]methyl]-N-cyclopropyl-2-furanmethanamine, bis oxalate salt A solution of 5-[(cyclopropylamino)methyl]-2-furanmethanol, oxalate salt (3.1 g) in water (5 ml) was added slowly to a solution of 2-aminoethanethiol hydrochloride (1.5 g) in concentrated hydrochloric acid below 10°. After 3 days at room temperature the solution was basified and dried with excess anhydrous sodium carbonate. The solid was extracted with isopropanol and evaporation of the extracts yielded a brown oil. A solution of this in ethanol was acidified with a solution of oxalic acid in ethanol to give the title compound (2.32 g) as a crystalline solid.

TLC (silica/methanol-0.88 ammonia 79:1) Rf 0.41.

C.
N,N'-bis-[2-[[5-[(Cyclopropylamino)methyl]-2-furanylmethyl]thio]ethyl]-2-nitro-1,1-ethenediamine A mixture of 5-[[(2-aminoethyl)thio]methyl]-N-cyclopropyl-2-furanmethanamine (1.67 g) and 1,1-bis-(methylthio)-2-nitroethene (0.61 g) was heated at 98°-100° for 3 hr. The oily residue was chromatographed (silica/methanol-0.88 ammonia 79:1) and the appropriate eluate evaporated to dryness to give the title compound (1.07 g) as an oil.

TLC (silica/methanol-0.88 ammonia 79:1) Rf 0.61.

NMR (CDCl$_3$)$\tau$: 8.6-9.2 m (8H); 7.95 m (2H); 7.0-7.5 brs (4H); 7.25 tr (4H); 6.65 brm, 6.26 s, 6.20 s (12H); 3.75-4.0 m (4H); 3.45 s (1H).

EXAMPLE 16

N,N'-bis-[2-[[5-[[Hydroxy(methyl)amino]methyl]-2-furanylmethyl]thio]ethyl]-2-nitro-1,1-ethenediamine

A.
5-[[Hydroxy(methyl)amino]methyl]-2-furanmethanol

A mixture of 2-furanmethanol (14.7 g), N-methylhydroxylamine hydrochloride (13.8 g) and aqueous formaldehyde (36%, 18 ml) was stirred at 0° hr and at room temperature for 4 hr. The solution was diluted with water (100 ml), excess sodium bicarbonate added and the solution extracted with ethyl acetate (4×100 ml). The combined ethyl acetate extracts were dried (sodium sulphate), filtered and the filtrate evaporated to give an oil which was distilled (6×10$^{-1}$ mm/200°-210°) to give the title compound (9.1 g).

TLC (silica/ether) Rf 0.2.

B.
5-[[2-Aminoethyl)thio]methyl]-N-hydroxy-N-methyl-2-furanmethanamine, dihydrochloride 5-[[Hydroxy(methyl)amino]methyl]-2-furanmethanol (7.85 g) was added to a stirred solution of 2-aminoethanethiol hydrochloride (5.68 g) in concentrated hydrochloric acid (15 ml) at 0° during 45 mins. After 48 hr at 0° the crystalline solid which separated was mixed with isopropanol (40 ml), filtered and crystallised from ethanol to give the title compound (9.1 g) m.p. 164°-165° dec.

C.
N,N'-bis-[2-[[5-[[Hydroxy(methyl)amino]methyl]-2-furanylmethyl]thio]ethyl]-2-nitro-1,1-ethenediamine A mixture of 5-[[(2-aminoethyl)thio]methyl]-N-hydroxy-N-methyl-2-furanmethanamine base (1.48 g) and 1,1-bis-(methylthio)-2-nitroethene (0.57 g) was heated at 98°-100° for 3 hr. The oily residue was chromatographed (silica/acetone) and the appropriate eluate evaporated to give the title compound (0.78 g) as an amber oil.

TLC (silica/acetone) Rf 0.35.

Found: C,47.9; H,6.5; N,13.7. C$_{20}$H$_{31}$N$_5$O$_6$S$_2$ requires: C,47.9; H,6.2; N,14.0%.

EXAMPLE 17

N-[3-[3-[(Dimethylamino)methyl]phenoxy]propyl]-N'-[2-[[5-[(methylamino)methyl]-2-furanylmethyl]thio]ethyl]-2-nitro-1,1-ethenediamine

C. N-Methyl-5-[[[2-[(1-methylthio-2-nitroethenyl)amino]ethyl]thio]methyl]-2-furanmethanamine, oxalate salt A solution of 2-[[5-[(methylamino)methyl]-2-furanylmethyl]thio]ethanamine (6.0 g) and 1,1-bis-(methylthio)-2-nitroethane (19.8 g) in dry dimethylformamide (150 ml) was stirred for 1 hour at 0° and for 5 hours at room temperature. A solution of oxalic acid (4.0 g) in dry dimethylformamide (16 ml) was added and the solid which formed during 18 hours was filtered, washed with dimethylformamide, ethanol and ether and dried. The solid was suspended in water (200 ml) at 55° and on cooling was filtered, washed with water and dried to give the title compound (3.25 g) m.p. 158°-160° dec.

B.
N-[3-[3-(Dimethylamino)methyl]phenoxy]propyl]-N'-[2-[[5-[(methylamino)methyl]-2-furanylmethyl]thio]ethyl]-2-nitro-1,1-ethenediamine A mixture of N-methyl-5-[[[2-[(1-methylthio-2-nitroethenyl)amino]ethyl]thio]methyl]-2-furanmethanamine (1.6 g) (prepared from the oxalate salt) and 3-(3-aminopropoxy)-N,N-dimethylbenzenemethanamine (1.15 g) was heated at 98°-100° for 3 hours. The oily product was chromatographed (silica/methanol-0.88 ammonia 79:1) and the appropriate eluate evaporated to dryness to give the title compound as a hydrate as an amber oil (2.12 g).

TLC (silica/methanol-0.88 ammonia 79:1) Rf 0.22.

NMR (CDCl$_3$)$\tau$: 8.18 br (1H); 7.85 m (2H); 7.75 s (6H); 7.58 s (3H); 7.30 tr (2H); 6.5-7.0 m, 6.60 s (6H); 6.31 s (4H); 5.94 tr (2H); 3.90 AB (2H); 3.46 s (1H); 3.0-3.3 m (3H); 2.80 tr (1H); −0.5 br (1H).

EXAMPLE 18

N-[2-[[5-[(Dimethylamino)methyl]-2-furanylmethyl]thio]ethyl]-N'-[3-[3-(dimethylamino)methyl]phenoxy]propyl]thiourea

A.
5-[[[2-(Isothiocyanato)ethyl]thio]methyl]-N,N-dimethyl-2-furanmethanamine A solution of carbon disulphide (4.2 g) in dry acetone (8 ml) was added dropwise to a solution of 5-[[(2-aminoethyl)thio]methyl]-N,N-dimethyl-2-furanmethanamine (10.71 g) in dry acetone (30 ml) during 15 minutes at −10° to 0°. To the stirred solution at −15° was added dropwise a solution of mercuric chloride (13.6 g) in dry acetone (20 ml) during 45 minutes. The solution was warmed to 0° and triethylamine (11.5 g) was added dropwise with stirring during 15 minutes. The mixture was refluxed for 45 minutes, the suspension filtered and the filtrate evaporated to dryness. The oily residue was dissolved in ether (150 ml), decolourising charcoal and excess anhydrous sodium sulphate were added and the suspension filtered after 2 hours. The filtrate was evaporated to dryness, the oily residue dissolved in ether and the solution chromatographed (alumina deactivated with water, 72.5 ml/kg/ether). The appropriate eluate was evaporated to give the title compound (5.05 g) as a brown oil.

TLC (alumina/ether) Rf 0.9.

B. N-[2-[[5-[(Dimethylamino)methyl]-2-furanylmethyl]thio]ethyl]-N'-[3-[3-[(dimethylamino)methyl]phenoxy]propyl]thiourea To a solution of 5-[[[2-(isothiocyanato)ethyl]thio]methyl]-N,N-dimethyl-2-furanmethanamine (0.77 g) in dry acetonitrile (3 ml) was added a solution of 3-(3-aminopropoxy)-N,N-dimethylbenzenemethanamine (0.63 g) in dry acetonitrile (3 ml). After 1 hour the solution was evaporated to dryness to give an oil which was chromatographed (silica/methanol-0.88 ammonia 79:1). The appropriate eluate was evaporated to dryness to give the title compound (1.25 g) as an oil.

TLC (silica/methanol-0.88 ammonia 79:1) Rf 0.45.

Found: C,59.2; H,7.9; N,12.0; S,13.5. $C_{22}H_{36}N_4O_2S_2$ requires: C,59.5; H,7.8; N,12.1; S,13.8%.

EXAMPLE 19

Pharmaceutical Compositions

| (a) Oral Tablets 50 mg | for 10,000 tablets |
|---|---|
| Active ingredient | 500 g |
| Anhydrous lactose U.S.P. | 2.17 kg |
| Sta-Rx 1500 Starch* | 300 g |
| Magnesium Stearate B.P. | 30 g |

*A form of directly compressible starch, supplied by A. E. Staley Mfg. Co. (London) Limited, Orpington, Kent.

The drug is sieved through a 250 μm sieve and then the four powders are intimately mixed in a blender and compressed between 0.5 mm diameter punches in a tabletting machine.

| (b) Injection for Intraveneous administration (50 mg in 2 ml) | |
|---|---|
| | % w/w |
| Active ingredient | 2.5 |
| Water for injections BP to | 100.0 |
| Dilute hydrochloric acid BP to | pH 5.0 |

The active ingredient is dissolved with mixing in the Water for Injection, adding the acid slowly until the pH is 5.0. The solution is sparged with nitrogen and is then clarified by filtration through a membrane filter of pore size 1.35 μm. It is packed into 2 ml glass ampoules (2.2 ml in each) and each ampoule sealed under an atmosphere of nitrogen. The ampoules are sterilsed in an autoclave at 121° for thirty minutes.

| (c) Oral Sustained Release Tablets 150 mg | for 10,000 tablets |
|---|---|
| Active ingredient | 1.50 kg |
| Cutina HR** | 0.40 kg |
| Anhydrous lactose U.S.P. | 2.060 kg |
| Magnesium Stearate BP | 40 g |

**Cutina HR is a grade of microfine hydrogenated castor oil supplied by Sipon Products Limited, London.

The active ingredient, anhydrous lactose and most of the Cutina HR are intimately mixed and then the mixture is moistened by mixing with a 10% solution of the remainder of the Cutina HR in Industrial Methylated Spirit OP 74. The moistened mass is granulated through a 1.2 mm aperture sieve and dried at 50° C. in a fluidised bed dryer. The granules are then passed through a 0.85 mm aperture sieve, blended with the magnesium stearate and compressed to a hardness of at least 10 kg (schleuniger tester) on a tabletting machine with 12.5 mm diameter punches.

We claim:

1. A compound of the formula (I)

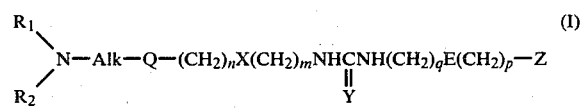

or a physiologically acceptable salt, N-oxide or hydrate thereof, in which Y represents =O, =S, =CHNO$_2$ or =NR$_3$ where R$_3$ represents hydrogen, nitro, cyano, lower alkyl, aryl, lower alkyl sulphonyl or aryl sulphonyl; R$_1$ and R$_2$, which may be the same or different each represents hydrogen, lower alkyl, cycloalkyl, lower alkenyl, aralkyl, hydroxy, lower trifluoroalkyl, lower alkyl substituted by hydroxy, lower alkoxy, amino, lower alkylamino or lower dialkylamino, or R$_1$ and R$_2$ together with the nitrogen atom to which they are attached form a pyrrolidine or piperidine ring;

Q represents a furan ring in which incorporation into the rest of the molecule is through bonds at the 2- and 5-positions;

X represents —CH$_2$—, —O— or —S—;

n represents zero, 1 or 2 except that n is not zero when X is —O—;

m represents 2, 3 or 4;

Alk represents a straight chain alkylene group of 1 to 3 carbon atoms;

q represents 2, 3 or 4 or can additionally represent zero or 1 when E is a —CH$_2$— group;

p represents zero, 1 or 2;

E represents —CH$_2$—, —O— or —S—; and

Z represents a phenyl ring optionally substituted by at least one of lower alkyl, hydroxy, lower alkyl hydroxy, amino, lower alkoxy or halo or a furyl, thienyl, pyridyl, imidazolyl, thiazolidinyl, oxazolidinyl or pyrimidinyl ring optionally substituted by lower alkyl optionally substituted by hydroxy or halo or Z represents the group

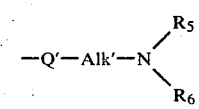

where Q' represents a 2,5-furan or thiophen ring or 1,3- or 1,4-benzene ring;

Alk' represents any of the groups defined for Alk; and R$_5$ and R$_6$, which may be the same or different, each represent any of the groups defined for R$_1$ and R$_2$; except that p is not zero when E is oxygen and Q' or Z is a furan or thiophen ring system.

2. A compound of the formula (II)

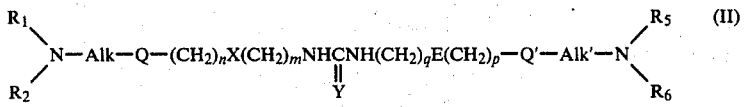

or a physiologically acceptable salt, N-oxide or hydrate thereof, in which Y represents =O, =S, =CHNO$_2$ or =NR$_3$ where R$_3$ represents hydrogen, nitro, cyano, lower alkyl, aryl, lower alkylsulphonyl or arylsulphonyl; R$_1$, R$_2$, R$_5$ and R$_6$, which may be the same or different, each represent hydrogen, lower alkyl, cycloalkyl, lower alkenyl, aralkyl, lower alkyl interrupted by an oxygen atom, or lower alkyl interrupted by a group

where R$_4$ represents hydrogen or lower alkyl or R$_1$ and R$_2$ together with the nitrogen atom to which they are attached or R$_5$ and R$_6$ together with the nitrogen atom to which they are attached form a pyrrolidine or piperidine ring;

Q represents a furan ring in which incorporation into the rest of the molecule is through bonds at the 2- and 5-positions;

Q' represents a furan or thiophen ring in which incorporation into the rest of the molecule is through bonds at the 2- and 5-positions, or a benzene ring in which incorporation into the rest of the molecule is through bonds at the 1- and 3-positions;

X and E which may be the same or different, each represent —CH$_2$—, —O— or —S—;

n and p, which may be the same or different, each represent zero, 1 or 2;

m and q, which may be the same or different, each represent 2, 3 or 4;

Alk and Alk', which may be the same or different, each represent a straight chain alkylene group of 1 to 3 carbon atoms; except that n is not zero when X is oxygen and p is not zero when E is oxygen and Q' is a furan or thiophen ring system.

3. A compound of the formula (III)

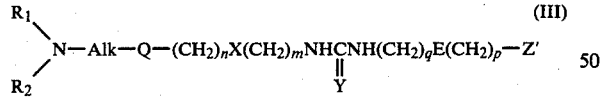

or a physiologically acceptable salt, N-oxide or hydrate thereof, in which Y represents =O, =S, =CHNO$_2$ or =NR$_3$ where R$_3$ represents hydrogen, nitro, cyano, lower alkyl, aryl, lower alkylsulphonyl or arylsulphonyl;

R$_1$ and R$_2$, which may be the same or different, each represent hydrogen, lower alkyl, cycloalkyl, lower alkenyl, aralkyl, lower alkyl interrupted by an oxygen atom, lower alkyl interrupted by

in which R$_4$ represents hydrogen or lower alkyl; or R$_1$ and R$_2$ together with the nitrogen atom to which they are attached form a pyrrolidine or piperidine ring;

Q represents a furan ring in which incorporation into the rest of the molecule is through bonds at the 2- and 5-positions;

X represents —CH$_2$—, —O— or —S—;

n represents zero or 1 except that n is not zero when X is oxygen;

m represents 2, 3 or 4;

Alk represents a straight chain alkylene group of 1 to 3 carbon atoms;

q represents 2, 3 or 4 or can additionally represent zero or 1 when E is a —CH$_2$— group;

p represents zero, 1 or 2;

E represents —CH$_2$—, —O—, or —S—; and

Z' represents a phenyl ring optionally substituted by at least one of lower alkyl, hydroxy, lower alkyl hydroxy, amino, lower alkoxy or halo or a furyl, thienyl, pyridyl, imidazolyl, thiazolidinyl, oxazolidinyl or pyrimidyl ring optionally substituted by lower alkyl optionally substituted by hydroxy or halo; except that p is not zero when E is oxygen and Z is furyl or thienyl.

4. A compound as claimed in claim 1 in which Y represents =O, =S, =CHNO$_2$, =NCN or =NSO$_2$CH$_3$;

R$_1$ and R$_2$, which may be the same or different, each represent hydrogen or lower alkyl or R$_1$ and R$_2$ together with the nitrogen atom to which they are attached form a pyrrolidine or piperidine ring;

Q represents a furan ring in which incorporation into the rest of the molecule is through bonds at the 2- and 5-positions;

X represents —O— or —S—;

n represents zero or 1;

m represents 2 or 3;

Alk represents —CH$_2$—;

q represents zero, 1, 2 or 3;

p represents zero, 1 or 2;

E represents —CH$_2$—, —O— or —S—; and

Z represents furyl, lower alkyl substituted imidazolyl, phenyl, hydroxyalkyl substituted furyl, pyridyl, hydroxyalkyl substituted

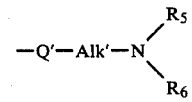

where Q' represents a furan or thiophen ring in which incorporation into the rest of the molecule is through bonds at the 2- and 5-position or a benzene ring in which incorporation into the rest of the molecule is through bonds at the 1- and 3-positions;

Alk' represents —CH$_2$—; and

R$_5$ and R$_6$ which may be the same or different, each represent hydrogen or lower alkyl or R$_5$ and R$_6$ together with the nitrogen atom to which they are attached form a pyrrolidine or piperidine ring.

5. The compound as claimed in claim 1 which is N-[2-[[5-[(dimethylaminomethyl]-2-furanylmethyl]thio]ethyl]-N'-[[2-(furanylmethyl)-thio]ethyl]-2-nitro-1,1-ethenediamine;

N-[3-[5-[(dimethylamino)methyl]-2-furanylmethoxy]propyl]-2-nitro-N'-[2-[(3-pyridinylmethyl)thio]ethyl]-1,1-ethenediamine;

N-[2-[[5-[(dimethylamino)methyl]-2-furanylmethyl]thio]ethyl]-N'-[3-[3-(hydroxymethyl)phenoxy]propyl]-2-nitro-1,1-ethenediamine;

N-[2-[[5-[(dimethylamino)methyl]-2-furanylmethyl]thio]ethyl]-2-nitro-N'-[2-[(3-pyridinylmethyl)thio]ethyl]-1,1-ethenediamine;

N,N'-bis-[2-[[5-[(methylamino)methyl]-2-furanylmethyl]thio]ethyl]-2-nitro-1,1-ethenediamine;

N-[2-[[5-[(dimethylamino)methyl]-2-furanylmethyl]thio]ethyl]-N'-[3-[3-[(dimethylamino)methyl]phenoxy]propyl]-2-nitro-1,1-ethenediamine;

N-[2-[[5-[(dimethylamino)methyl]-2-furanylmethyl]thio]ethyl]-N'-[2-[[5-[(dimethylamino)methyl]-2-thienylmethyl]thio]ethyl]-2-nitro-1,1-ethenediamine;

N-[2-[[5-[(dimethylamino)methyl]-2-furanylmethyl]thio]ethyl]-N'-[2-[[5-[(methylamino)methyl]-2-furanylmethyl]thio]ethyl]-2-nitro-1,1-ethenediamine;

N-[2-[[5-[(dimethylamino)methyl]-3-furanylmethyl]thio]ethyl]-N'-[2-[[5-[[hydroxy(methyl)amino]methyl]-2-furanylmethyl]thio]ethyl]-2-nitro-1,1-ethenediamine;

N-[3-[3-[(dimethylamino)methyl]phenoxy]propyl]-N'-[2-[[5-[(methylamino)methyl]-2-furanylmethyl]thio]ethyl]-2-nitro-1,1-ethenediamine;

N''-cyano-N-[3-[3-[(dimethylamino)methyl]phenoxy]propyl]-N'-[2-[[5-[(1-pyrrolidinyl)methyl]-2-furanylmethyl]thio]ethyl]guanidine;

N-[2-[[5-[(dimethylamino)methyl]-2-furanylmethyl]thio]ethyl]-2-nitro-N'-[3-[3-[(1-pyrrolidinyl)methyl]phenoxy]propyl]-1,1-ethenediamine.

6. The compound of claim 5 which is N-[2-[[5-[(dimethylamino)methyl]-2-furanylmethyl]thio]ethyl]-N'-[3-[3-[(dimethylamino)methyl]phenoxy]propyl]-2-nitro-1,1-ethenediamine.

7. A pharmaceutical composition comprising an effective amount of at least one compound as defined in claim 1 together with at least one pharmaceutically acceptable carrier or diluent and optionally an effective amount of at least one other active ingredient.

8. A method of treating a condition mediated through histamine $H_2$-receptors which comprises administering to a patient an effective amount of a compound as defined in claim 1 to relieve said condition.

* * * * *